United States Patent
Brainard et al.

(10) Patent No.: US 8,366,755 B2
(45) Date of Patent: Feb. 5, 2013

(54) PHOTORECEPTOR SYSTEM FOR MELATONIN REGULATION AND PHOTOTHERAPY

(75) Inventors: George Brainard, Haddonfield, NJ (US); Gena Glickman, San Diego, CA (US)

(73) Assignee: Progressive Lighting and Radiometrics, LLC, Haddonfield, NJ (US)

(*) Notice: Subject to any disclaimer, the term of this patent is extended or adjusted under 35 U.S.C. 154(b) by 333 days.

(21) Appl. No.: 12/657,533

(22) Filed: Jan. 22, 2010

(65) Prior Publication Data
US 2010/0214559 A1 Aug. 26, 2010

Related U.S. Application Data

(63) Continuation of application No. 09/853,428, filed on May 10, 2001, now Pat. No. 7,678,140.

(51) Int. Cl.
A61N 5/06 (2006.01)

(52) U.S. Cl. ........................................ 607/88

(58) Field of Classification Search ............ 607/88; 356/213, 215, 221, 218, 922 D
See application file for complete search history.

(56) References Cited

U.S. PATENT DOCUMENTS

| | | | |
|---|---|---|---|
| 3,445,153 A | 5/1969 | Marks et al. |
| 4,547,074 A | 10/1985 | Hinoda et al. |
| 4,858,609 A | 8/1989 | Cole |
| 5,083,858 A | 1/1992 | Girerd |
| 5,170,035 A | 12/1992 | Webster et al. |
| 5,235,178 A | 8/1993 | Hegyi |
| 5,265,598 A | 11/1993 | Searfoss et al. |
| 5,274,403 A | 12/1993 | Gott |
| 5,447,527 A | 9/1995 | Waldman |
| 5,545,192 A | 8/1996 | Czeisler et al. |
| 5,562,719 A | 10/1996 | Lopez-Claros |
| 5,645,578 A | 7/1997 | Daffer et al. |
| 5,648,653 A | 7/1997 | Sakamoto et al. |
| 5,824,024 A | 10/1998 | Dial |
| 5,855,595 A | 1/1999 | Fujishima et al. |
| 5,923,398 A | 7/1999 | Goldman |
| 6,069,164 A | 5/2000 | Lewy et al. |
| 6,235,046 B1 | 5/2001 | Gerdt |
| 6,271,913 B1 | 8/2001 | Jung et al. |
| 6,554,439 B1 | 4/2003 | Teicher et al. |

OTHER PUBLICATIONS

Aggelopoulos et al, Responses of neurones of the rat suprachiasmatic nucleus to retinal illumination under photopic and scotopic conditions, J Physiol, 523:211-222 (2000).

Ahmad et al, HY4 gene of *A. thaliana* encodes a protein with characteristics of a blue-light photoreceptor, Nature, 366: 162-166 (1993).

Arendt J, Melatonin [Review], Clin Endocrinol, 29:205-229 (1988).

Arendt J. Melatonin and the pineal gland: influence on mammalian seasonal and circadian physiology. Rev Reprod, 3:13-22 (1998).

Boettner et al, Transmission of the ocular media, Invest Ophthalmol Vis Sci, 1(6):776-783 (1962).

(Continued)

*Primary Examiner* — Roy Gibson
(74) *Attorney, Agent, or Firm* — Goodwin Procter LLP; Richard W. Thill

(57) ABSTRACT

The present invention involves a light system for stimulating or regulating neuroendocrine, circadian, and photoneural systems in mammals based upon the discovery of peak sensitivity ranging from 425-505 nm; a light meter system for quantifying light which stimulates or regulates mammalian circadian, photoneural, and neuroendocrine systems. The present invention also relates to translucent and transparent materials, and lamps or other light sources with or without filters capable of stimulating or regulating neuroendocrine, circadian, and photoneural systems in mammals. Additionally, the present invention involves treatment of mammals with a wide variety of disorders or deficits, including light responsive disorders, eating disorders, menstrual cycle disorders, non-specific alerting and performance deficits, hormone-sensitive cancers, and cardiovascular disorders.

4 Claims, 19 Drawing Sheets

OTHER PUBLICATIONS

Bolvin et al, Dose-response relationships for resetting of human circadian clock by light, Nature, 379: 540-542 (1996) (Abstract Only).

Brainard et al, Action spectra for circadian and neuroendocrine regulation in mammals. In: Measurements of Optical Radiation Hazards (Matthes R. Sliney D, Didormenico S, Murray P. Phillips R. Wengraitis S, eds), pp. 131-142. Munchen, Germany:ICNIRP (1999).

Brainard et al, Action Spectrum for Melatonin Regulation in Humans, Presented at 8th European Pineal Society Colloqiurn, Tours, France, Jul. 3-7.

Brainard et al, Action Spectrum for Melatonin Regulation in Humans: Evidence for a Novel Circadian Photoreceptor, J. of Neuroscience, 21(6):6405-6412 (2001).

Brainard et al, Circadian photoreception in humans: action spectrum for melatonin suppression, Presented at 7th Meeting of the Society for Research on Biological Rhythms, Jacksonville, FL, May 10-13.

Brainard et al, Development of an Action Spectrum for Melatonin Regulation: Potential Relevance to Light Therapy, Soc Light Treat Biol Rhythms Abstract 11:1 (1999).

Brainard et al, Dose-response relationship between light irradiance and the suppression of melatonin in human volunteers, Brain Res, 454:212-218 (1988) (Abstract Only).

Brainard et al, Human melatonin regulation is not mediated by the three cone photopic visual system, J Clin Endocrinol Metab, 86(1):433-436 (2001).

Brainard et al, Photic regulation of melatonin humans: ocular and neural signal transduction, J Biol Rhythms. 12(6):537-546 (1997).

Brainard et al, Section 824.1—Circadian Photoreception: Action Spectrum for Melatonin Regulation in Humans, Sociate for Neuroscience, vol. 25 (1999).

Brainard et al, Section SAM-C4, Development of An Action Spectrum for Melatonin Suppression in Humans, Photochem Photobiol. (1959).

Brainard et al. The effect of polarized versus non-polarized light on melatonin regulation in humans, Photochem Photobiol, 71(6):766-770 (2000).

Brainard et al, The suppression of pineal melatonin content and N-acetyltransferase activity by different light irradiances in the Syrian hamster: a dose-response relationship, Endocrinology, 113(1):293-296 (1983).

Bronstein et al, Action spectrum of the retinal mechanism mediating nocturnal light-induced suppression of rat pineal gland N-acytyltransferase, Brain Res, 406:352-356 (1987).

Coohill, Action spectra again?, Photochemistry and Photobiology, 54(5):859-870 (1991).

Czeisler et al, Bright light resets the human circadian pacemaker independent of the timing of the sleep-wake cycle. Science, 233:667-671 (1986) (Abstract Only).

Czeisler et al, Suppression of melatonin secretion in some blind patients by exposure to bright light, N Engl J Med. 332:6-11 (1995).

Davis et al, Radioimmunoassay data processing with a small programmable calculator, Journal of Immunoassay, 1(1):15-25 (1960).

Dkhissi-Benyahya et al, Effects of irradiance and stimulus duration on early gene expression (fos) in the suprachiasmatic nucleus: temperature summation and reciprocity, J Neurosci, 20:7790-7797 (2000).

European Examination Report dated Oct. 13, 2003 for EP Application No. 01975620 0.

Foster et al, Circadian photoreception in the retinally degenerate mouse (*rd/rd*), J Comp Physiol A, 169:39-50 (1991).

Freedman et al, Regulation of mammalian circadian behavior by non-rod, non-cone, ocular photoreceptors, Science, 284:502-504 (1999).

Gaddy et al, Pupil size regulation of threshold of light-induced melatonin suppression, J Clin Endocrinol Metab, 77(5):1398-1401 (1993).

Goto et al, The influence of different light intensities on pineal melatonin content in the retinal degenerate C3H mouse and the normal CBA mouse, Neurosci Lett, 108:267-272 (1990) (Abstract Only).

Griffin et al, Light-independence role of CRY1 and CRY2 in the mammalian circadian clock, Science, 286:768-771 (1999).

International Preliminary Examination Report dated Mar. 28, 2003 for PCT Application No. PCT/US01/15272.

International Search Report dated Sep. 24, 2001 for PCT Application No. PCT/US01/15272.

Klein et al, Rapid light-induced decrease in pineal serotonin Nacetyltransferase activity. Science, 177:532-533 (1972) (Abstract Only).

Lerman, Chemical and physical properties of the normal and aging lens: Spectroscopic (UV. fluorescence, phosphorescence, and NMR) analyses, Am J Opt Physiol Optics, 64(1).11-22 (1987).

Lewy et al, Light suppresses melatonin secretion in humans, Science, 210:1267-1269 (1980).

Lipson, Action Spectroscopy: Methodology. In: Organic Photochemistry and Photobiology, New York CRCPress, pp. 1257-1266 (1994).

Lucas et al, Neither functional rod photoreceptors nor rod or cone outer segments are required for the photic inhibition of pineal melatonin, Endocrinology, 140:1520-1524 (1999).

McIntyre et al, Human Melatonin Suppression by Light is Intensity Dependent, J. of Pineal research, 8:149-186 (1989).

Miyamoto et al, Vitamin $B_2$-based blue-light photoreceptors in the retinohypothalamic tract as the photoactive pigments for setting the circadian clock in mammals. PNAS. 95:6097-6102 (1996).

Moore, Organization and function of a central nervous system circadian oscillator: the suprachiasmatic hypothalamic nucleus, FASEB, 42:2783-2789 (1983).

Morin, The circadian visual system, Brain Res Brain Res Rev, 19:102-127 (1994).

Nelson et al, Comparison of visual sensitivity for suppression of pineal melatonin and circadian phase-shifting in the golden hamster, Brain Res, 554:272-277 (1991).

Oren, Humoral phototransduction: blood is a messenger, The Neuroscientist, 2(4):207-210 (1996).

Partridge et al, A new template fo rhodopsin (vitamin $A_1$ based) visual pigments, Vision Res, 31:6:619-630 (1991).

Pevet et al, Photoperiod perception in the blind mole rat (Spalax ehrenbergi, Nehring) involvement of the Hardenan gland, atrophied eyes, and melatonin, J Exp Zool. 232:41-50 (1984).

Podolin et al, The suppression of nocturnal pineal melatonin in the Syrian hamster: dose-response curves at 500 and 360 nm, Endocrinology, 121(1):268-270 (1987).

Provencio et al, A novel human opsin in the inner retina, J Neurosci. 20:600-605 (2000).

Provencio et al, Circadian rhythms in mice can be regulated by photoreceptors with cone-like characteristics, Brain Res, 694:183-190 (1995).

Provencio et al, Melanopsin: an opsin in melanophores, brain, and eye, PNAS, 95:340-345 (1998).

Reiter, Pineal melatonin: cell biology of its synthesis and of its physiological interactions, Endocr Rev, 12(2):151-160 (1991).

Rollag et al, Radioimmunoassay of serum concentrations of melatonin in sheep exposed to different lighting regimens, Endocrinology, 98(2):482-489 (1976).

Ruberg et al, Melatonin regulation in humans with color vision deficiencies, J Clin Endocrinol Metab, 81(8):2980-2985 (1986).

Schwartz et al, A discrete lesion of ventral hypothalamus and optic chiasm that disturbed the daily temperature rhythm, J Neurol, 233:1-4 (1986) (Abstract Only).

Soni et al. A novel and ancient vertebrate opsin, FEBS Lett, 406:279-283 (1997).

Stanewsky et al. The $cry^b$ mutation identifies cryptochrome as a circadian photoreceptor in *Drosophila*, Cell, 95:681-692 (1998).

Stockman et al, The spectral sensitivity of the human short-wavelength sensitive cones derived from thresholds and color matches, Vision research 39:2901-2927 (1999).

Sun et al, Peropsin, a novel visual pigment-like protein located in the apical microvilli of the retinal pigment epithelium, PNAS, 94:9893-9898 (1997).

Takahashi et al, Spectral sensitivity of a novel photoreceptive system mediating entrainment of mammalian circadian rhythms, Nature 308:186-188 (1984).

Thresher et al, Role of mouse cryptochrome blue-light photoreceptor in circadian photoresponse, Sciences, 282:1490-1494 (1998).

van der Horst et al, Mammalian Cry1 and Cry2 are essential for maintenance of circadian rhythms, Nature, 398:627-630 (1999).

von Schantz et al, Recent developments in circadian photoreception: more than meets the eye. Invest Ophthalmol Vis Sci, 41:1605-1607 (2000).

Waldhauser et al, Daily and annual rhythms in human melatonin secretion: role in puberty control, Ann NY Acad Sci, 453:205-214 (1985).

Wang et al, Ocular regulation of the human pineal gland: the significance of total retinal exposure for melatonin suppression, Biologic Effects of Light 1998, Kluwer Academic Publishers., pp. 367-374 (1999).

Webb et al, Photoreceptor damage and eye pigmentation: influence on the sensitivity of rat pineal N-acetyltransferase activity and melatonin levels to light at night, Neuroendocrinology, 40:205-209 (1985).

Wehr TA, The durations of human melatonin secretion and sleep respond to changes in daylength (photoperiod), J Clin Endocrinol Metab. 73(6):1276-1280 (1991).

Written Opinion dated Jul. 9, 2002 for PCT Application No. PCT/US01/15272.

Yoshimura et al, Spectral sensitivity of photoreceptors mediating phase-shifts of circadian rhythms in retinally degenerate CBA/J (rd/rd) and normal CBA/N (+/+) mice, J Comp Physiol A, 178 797-802 (1996).

Zeitzer et al, Photopic transduction implicated in human circadain entrainment, Neurosci Lett, 232:135-138 (1997).

Zeitzer et al, Sensitivity of the human circadian pacemaker to nocturnal light: melatonin phase resetting and suppression, J Physiol, 526:695-702 (2000).

US 8,366,755 B2

PHOTORECEPTOR SYSTEM FOR MELATONIN REGULATION AND PHOTOTHERAPY

CROSS REFERENCE TO RELATED APPLICATIONS AND INCORPORATION BY REFERENCE

This application is a continuation of non-provisional application of George Brainard and Gena Glickman, Ser. No. 09/853,428, filed on May 10, 2001, entitled: Photoreceptor System For Melatonin Regulation And Phototherapy, now U.S. Pat. No. 7,678,140. The entire disclosure of parent patent application of George Brainard and Gena Glickman, Ser. No. 09/853,428, filed on May 10, 2001, is incorporated herein by reference.

This application is related to, claims priority under and claims the benefit of the earliest available effective filing dates from the following listed applications:

Non-provisional application of George Brainard and Gena Glickman, Ser. No. 09/853,428, filed on May 10, 2001, entitled: Photoreceptor System For Melatonin Regulation And Phototherapy;

Provisional Application by George C. Brainard, Application No. 60/228,493, filed on Aug. 28, 2000, entitled: A New Photoreceptor System for Melatonin Regulation; and, Provisional Application by George Brainard, Application No. 60/203,308, filed on May 10, 2000, entitled: Light System, Meter System, and Materials for Stimulating Circadian and Neuroendocrine Systems.

GOVERNMENT RIGHTS IN THE APPLICATION

This invention was made with government support under grants from NIH RO1NS36590 awarded by the National Institutes of Health.; NSBIR/NASA HPF.002.08 (to GCB) awarded by the National Space Biology Research Institute in cooperation with the National Aeronautics and Space Administration; NSF IBN9809916 awarded by the National Science Foundation; and DOD RO70HY (to MDR) awarded by the Department of Defense. The government has certain rights in the invention.

FIELD OF THE INVENTION

The present invention generally relates to the fields of neurology, neuroscience, and endocrinology and to light systems, light meters, lamps, filters, transparent and translucent materials, and methods of treating a variety of mammalian disorders and, more particularly to a light system for stimulating or regulating neuroendocrine, circadian, and photoneural systems in mammals based upon the discovery of peak sensitivity ranging from 425-505 nm; a light meter system for quantifying light which stimulates mammalian circadian, photoneural, and neuroendocrine systems; translucent and transparent materials, and lamps or other light sources with or without filters stimulating or regulating neuroendocrine, circadian, and photoneural systems in mammals; and treatment of mammals with a wide variety of disorders or deficits, including light responsive disorders, eating disorders, menstrual cycle disorders, non-specific alerting and performance deficit, hormone-sensitive cancers, and cardiovascular disorders.

BACKGROUND OF THE INVENTION

Light is the primary stimulus for regulating circadian rhythms, seasonal cycles, and neuroendocrine responses in many species including humans (Klein et al., 1991; Wehr, 1991). Further, clinical studies have demonstrated that light therapy is effective for treating selected affective disorders, sleep problems, and circadian disruptions (Wetterberg, 1993; Lam, 1998). Previously, the ocular photoreceptors which transduce light stimuli for circadian regulation and the clinical benefits of light therapy have been unknown.

Nonetheless, scientists have been deeply involved in elucidating the physiologic and functional anatomic features associated with light and vision. In fact, the underlying neuroanatomy and neurophysiology which mediate vision have been studied extensively over the past two centuries. More recently, the retinohypothalamic tract (RHT), a distinct neural pathway which mediates circadian regulation by environmental light, has been shown to project from the retina to the suprachiasmatic nuclei (SCN) in the hypothalamus. (Moore R Y, Lenn N J. A retinohypothalamic projection in the rat. *J Comp Neurol* 146:1-14, 1972; Moore R Y (1983) Organization and function of a central nervous system circadian oscillator: the suprachiasmatic hypothalamic nucleus. Federation Proceedings 42:2783-2789; Klein D C, Moore R Y, Reppert S M, eds. *Suprachiasmatic Nucleus: The Mind's Clock*. Oxford: Oxford University Press, 5-456, 1991; Morin L P (1994) The circadian visual system. Brain Res Brain Res Rev 19:102-127). By this pathway, light and dark cycles are perceived through the mammalian eyes, entrain SCN neural activity and, in turn, entrain the rhythmic secretion of melatonin from the pineal gland. In virtually all species, melatonin secretion is high during the night and low during the day (Reiter, 1991; Arendt, 1998).

In addition to entraining pineal rhythms, light exposure can acutely suppress melatonin secretion (Rollag and Niswender, 1976; Lewy et al., 1980). A well-defined multisynaptic neural pathway extends from the SCN to the pineal gland, which transmits information about light and circadian time for entraining the rhythmic production and secretion of the hormone melatonin. (Moore R Y, Lenn N J. *J Comp Neurol* 146:1-14, 1972; Klein D C et al., eds. *Suprachiasmatic Nucleus: The Mind's Clock*. 5-456, 1991; Schwartz W J, Busis N A, Hedley-Whyte E T. A discrete lesion of ventral hypothalamus and optic chiasm that disturbed the daily temperature rhythm. *J Neurol* 233:1-4, 1986; Arendt J. Melatonin and the pineal gland: influence on mammalian seasonal and circadian physiology. *Rev Reprod* 3: 13-22, 1998). In addition to synchronizing pineal indolamine circadian rhythms, ocular exposure to light during the night can acutely suppress melatonin synthesis and secretion (Klein D C, Weller J L (1972) Rapid light-induced decrease in pineal serotonin N-acetyltransferase activity. Science 177:532-533; Lewy A J, Wehr T A, Goodwin F K, Newsome D A, Markey S P (1980) Light suppresses melatonin secretion in humans. Science 210: 1267-1269). Light-induced melatonin suppression is a well-defined, broadly used marker for photic input to the RHT and SCN (Klein D C, 1991; Arendt J (1998) Melatonin and the pineal gland: influence on mammalian seasonal and circadian physiology. Rev Reprod 3:13-22; Brainard G C, Rollag M D, Hanifin J P (1997) Photic regulation of melatonin in humans: ocular and neural signal transduction. J Biol Rhythms 12:537-546; Lucas R J, Foster R G (1999) Neither functional rod photoreceptors nor rod or cone outer segments are required for the photic inhibition of pineal melatonin. Endocrinology 140:1520-1524).

Previously, it has not been known what photoreceptors transduce light stimuli for circadian regulation. Studies on animals with hereditary or light-induced retinal degeneration have raised the possibility that neither the rods nor the cones used for vision participate in light-induced melatonin suppression, circadian locomotor phase-shifts, or photoperiodic responses (Lucas, 1999; Webb S M, Champney T H, Lewinski A K, Reiter R J (1985) Photoreceptor damage and eye pigmentation: influence on the sensitivity of rat pineal N-acetyltransferase activity and melatonin levels to light at night. Neuroendocrinology 40:205-209; Goto M, Ebihara S (1990) The influence of different light intensities on pineal melatonin content in the retinal degenerate C3H mouse and the normal CBA mouse. Neurosci Lett. 108:267-272; Foster R G, Provencio I, Hudson D, Fiske S, DeGrip W, Menaker M (1991) Circadian photoreception in the retinally degenerate mouse (rd/rd). J Comp Physiol [A] 169:39-50; Freedman M S, Lucas R J, Soni B, von Schantz M, Munoz M, David-Gray Z, Foster R G (1999) Regulation of mammalian circadian behavior by non-rod, non-cone, ocular photoreceptors. Science 284:502-504). Studies using rodents with retinal degeneration suggest that neither the rods nor cones used for vision participate in light-induced melatonin suppression, circadian phase-shifts, or photoperiodic responses (Pevet et al., 1984; Webb et al., 1985; Foster et al., 1991). Furthermore, enucleation of rod-less, cone-less transgenic mice abolishes light-induced circadian phase-shifts and melatonin suppression (Lucas and Foster, 1999; Freedman et al., 1999). Recently, light-induced melatonin suppression and circadian entrainment have been demonstrated in humans with complete visual blindness (Czeisler C A, Shanahan T L, Klerman E B, Martens H, Brotman D J, Emens J S, Klein T, Rizzo J F, III (1995) Suppression of melatonin secretion in some blind patients by exposure to bright light. N Engl J Med 332:6-11) and with specific color vision deficiencies. (Ruberg, 1996). The study on humans with color vision deficiencies showed that protanopic and deuteranopic subjects who lacked functioning long wavelength-sensitive cones (red, or L cones), and middle wavelength cone photoreceptors (green, or M cones), exhibited normal light-induced melatonin suppression and entrainment of the melatonin rhythm (Ruberg F L, Skene D J, Hanifin J P, Rollag M D, English J, Arendt J, Brainard G C (1996) Melatonin regulation in humans with color vision deficiencies. J Clin Endocrinol Metab 81:2980-2985). Thus, by themselves, neither the red nor green cone system could be the primary input for melatonin regulation, at least in humans with color vision deficiencies. Together, the results from human and animal circadian studies on different forms of visual blindness suggest that melatonin regulation by light is controlled, at least in part, by photoreceptors which differ from the photoreceptors that mediate vision.

Recent studies with various vertebrate species have identified several new molecules which may serve as circadian photopigments. These putative photopigments include both opsin-based molecules, such as vertebrate ancient (VA) opsin and melanopsin, as well as non-opsin molecules like the cryptochromes (Soni B G, Foster R G (1997) A novel and ancient vertebrate opsin. FEBS Lett 406:279-283; Provencio I, Jiang G, De Grip W J, Hayes W P, Rollag M D (1998) Melanopsin: an opsin in melanophores, brain, and eye. Proc Natl Acad Sci USA 95:340-345; Miyamoto Y, Sancar A (1998) Vitamin B2-based blue-light photoreceptors in the retinohypothalamic tract as the photoactive pigments for setting the circadian clock in mammals. Proc Natl Acad Sci USA 95:6097-6102). Among these new photopigments, only melanopsin has been specifically localized to the human retina. (Provencio I, Rodriguez I R, Jiang G, Hayes W P, Moreira E F, Rollag M D (2000) A novel human opsin in the inner retina. J Neurosci 20:600-605). The molecular identification of these candidate photopigments and their localization in the retina and/or neural components of the circadian system make them well-suited to act as circadian phototransducers. Functional data confirming their direct role in circadian photoreception, however, have been lacking.

The present invention required determining whether or not the three cone system, which supports photopic (daytime) vision, was also the primary input for pineal melatonin suppression in humans with normal, healthy eyes. The peak wavelength sensitivity of the photopic visual system is near 555 nm. (Rodieck R W (1998) The First Steps in Seeing, Sunderland, Mass.: Sinauer Associates, Inc.). If melatonin regulation were mediated primarily by the three cone photopic visual system, then 555 nm light would be the most potent wavelength for regulating melatonin secretion.

In the present invention, data show that 505 nm is approximately four times stronger than 555 nm in suppressing melatonin. These results demonstrate that the ocular photoreceptor primarily responsible for pineal melatonin regulation in humans, is not the cone system that is believed to mediate photopic vision. This present invention involved the first test of a specific photoreceptor system for melatonin regulation in humans with healthy, intact eyes.

Developing an action spectrum is a fundamental means for determining the input physiology for the circadian system. This photobiological technique has high utility for 1) defining the relative effectiveness of photons at different wavelengths for eliciting a biological response, and 2) identifying the specific photopigment involved in that response. (Lipson, 1994; Coohill, 1999). The specific aim of the present study was to characterize the wavelength sensitivity of the photoreceptor system responsible for providing circadian input to the human pineal gland by establishing an action spectrum for light-induced melatonin suppression. The experiments defined an action spectrum that fits a retinaldehyde opsin template and identified 446-477 nm as the most potent wavelength region for regulating melatonin. Univariance among the eight fluence-response curves suggests that a single photopigment is primarily responsible for melatonin suppression. These results suggest that there is a novel photopigment in the human eye which mediates circadian photoreception.

Light as a Therapeutic Stimulus

Numerous studies have shown that environmental light is the primary stimulus for regulating circadian rhythms, seasonal cycles, and neuroendocrine responses in many mammalian species including humans (Klein et al., 1991; Morin, 1994; Czeisler, 1995). During the past 20 years, studies have tested the use of light for treating fall and winter depression (Seasonal Affective Disorder or SAD), nonseasonal depression, sleep disorders, menstrual dysfunction, and eating disorders. In addition, investigators are exploring the use of light for re-entraining human circadian physiology relative to the challenge of shift work or intercontinental air travel. A Congressional report estimated that there are 20 million shift workers in the United States. (US Congress, 1991). The two most common problems associated with shift work are reduced alertness on the job and reduced sleep quality after work. In addition, shift workers have increased health problems including higher risk of cardiovascular disease and gastrointestinal distress as well as cognitive and emotional problems. Chronic desynchronization of the circadian system is cited as one of the causes for these problems. (US Congress, 1991).

Light is known to be a potent stimulus for entraining and phase-shifting circadian rhythms in many species, including humans. (Czeisler et al., 1986; Klein et al., 1991). The circadian response to light is dependent on the stimulus intensity, wavelength and time of delivery. A phase-response curve (PRC) describes light-induced shifts in rhythms relative to the circadian phase when the light is given, and PRCs to light share similarities across many species.

Working from the human PRC to light, some investigators have tested strategies of light treatment to improve circadian entrainment thereby enhancing performance, alertness, and health in shift workers. Studying simulated shift work, different groups of investigators have shown that workers had accelerated circadian re-entrainment, enhanced alertness, and improved sleep quality after treatment with bright light (2,000 lux to 12,000 lux) versus dimmer light (10 lux to 150 lux).

Light Stimulation of the Circadian and Neuroendocrine Systems

Over the last two centuries, extensive research has elucidated the neuroanatomy and neurophysiology which support the sensory capacity of vision in mammals. More recently, animal studies have demonstrated a neural pathway, named the retinohypothalamic tract (RHT), which projects from the retina into the hypothalamus. (Moore and Lenn, 1972; Klein et al., 1991). Information about light is transmitted from the retina to the hypothalamic suprachiasmatic nuclei (SCN) which are fundamental circadian oscillators that regulate daily rhythms. (Klein et al., 1991). The pathways supporting vision and circadian regulation are anatomically separate, but there may be a link between these systems by a projection from the intergeniculate leaflet to the SCN. (Morin, 1994). Although the detailed neuroanatomy of the circadian system primarily has been determined with animal studies, parallel clinical and post-mortem studies suggest that humans have a similar circadian neuroanatomy. (Schwartz et al., 1986).

The circadian system controls daily rhythms of sleep, wakefulness, body temperature, hormonal secretion, and other physiological parameters. (Klein et al., 1991; Morin, 1994; Lam, 1998). There is considerable evidence from studies on mammals that the circadian and neuroendocrine effects of light are mediated via photoreceptive physiology in the eye as opposed to photoreceptive physiology in the skin or some other part of the body. A study by Campbell and Murphy (1998), however, reported that a 3 hour bright light pulse of 13,000 lux delivered to the backs of the knees of human subjects systematically reset circadian rhythms of body temperature and melatonin. In contrast, two recent studies failed to elicit acute melatonin suppression with similar bright light exposure to the backs of the knees in healthy humans and an attempt to replicate Campbell and Murphey's findings failed to demonstrate a phase-shift after light exposure to the back of the. Further work is needed to determine whether or not the eyes are the exclusive sites for circadian photoreception in humans and other mammalian species. Data suggest that the eyes are the primary (if not exclusive) site for circadian and neuroendocrine phototransduction. Although light is the principal stimulus for regulating the circadian system, other external stimuli such as sound, temperature, social cues and conditioning may also influence physiological timing functions.

Light Regulation of Melatonin

A well-defined neural pathway carries photic information about light extends from the SCN to the pineal gland via a multisynaptic pathway with connections being made sequentially in the paraventricular hypothalamus, the upper thoracic intermediolateral cell column, and the superior cervical ganglion. (Moore, 1983). By way of this neuroanatomy, cycles of light and dark which are perceived through the eyes entrain SCN neural activity which, in turn, entrains the rhythmic synthesis and secretion of melatonin from the pineal gland. In virtually all species including humans, high levels of melatonin are secreted during the night and low levels are secreted during the day.

In addition to entraining the melatonin circadian rhythm, light can acutely suppress melatonin secretion. Specifically, exposure of the eyes to light during the night causes a rapid decrease in the high activity of the pineal enzyme serotonin-N-acetyltransferase and subsequent inhibition of synthesis and secretion of melatonin. The acute light-induced suppression of melatonin was first observed in rats and later in humans (Klein and Weller, 1972; Lewy et al., 1980). This response has been used as a tool by the PI (GCB) and many other investigators to help determine the ocular, neural and biochemical physiology for melatonin regulation. (Klein et al., 1991; Brainard et al., 1997). In addition, seasonal changes in photoperiod length alters the duration of the elevated melatonin production. Specifically, in a number of mammalian species including humans, the duration of increased nocturnal melatonin secretion is shorter in the summer due to shortened night time periods. In summary, many studies have shown that light stimuli are the strongest and most consistent regulators of melatonin. In addition, certain drugs can powerfully impact melatonin secretion, while other non-photic and non-pharmacologic stimuli that may modify melatonin levels include body posture and exercise.

Phototransduction and Action Spectrum Analysis

The overall aim of the present invention is the identification of the photoreceptor(s) for applications in the areas of circadian regulation, neuroendocrine regulation, and the clinical benefits of light therapy in humans. Fundamentally, all photobiological responses are mediated by specific organic molecules that absorb photons and then undergo physical-chemical changes which, in turn, lead to broader physiological changes within the organism. This photobiological process is termed phototransduction and the organic molecules which absorb light energy to initiate photobiological responses are called photopigments. Generally, these photoactive molecules do not absorb energy equally across the electromagnetic spectrum. Each photoreceptor molecule or complex has a characteristic absorption spectrum which depends on its atomic structure. An action spectrum is one of the main tools for identifying the photopigment which initiates a photobiological response. The simplest definition of an action spectrum is the relative response of an organism to different wavelengths. (Lipson, 1994; Coohill, 1999).

Photobiologists have evolved a refined set of practices and guidelines for determining analytical action spectra which are applicable to all organisms from plants to humans. (Coohill, 1991; Lipson, 1994). Analytical action spectra are developed using two or more monochromatic light stimuli with half-peak bandwidths of 15 nm or less. Generally, these action spectra are determined by establishing a set of dose-response curves (fluence-response curves) at different wavelengths for a specific biological response. The action spectrum is then formed by plotting the reciprocal of incident photons required to produce the criterion biological response versus wavelength. This fundamental photobiological technique has high utility for 1) defining the relative effectiveness of different wavelengths for eliciting a biological response, and 2) identifying the specific photosensitive molecules involved in biological responses.

Action Spectra for Circadian Regulation in Rodents

As in other fields of photobiology, the initial attempts to define circadian and neuroendocrine responses to wavelength began with polychromatic action spectra which tested broader bandwidths of light in various rodent species (Coohill, 1991). These polychromatic action spectra were published mainly during the early 1970's through the mid 1980's and were reasonably consistent in indicating that the spectral region between 450 nm and 550 nm provides the strongest stimulation of circadian and neuroendocrine responses in rodents (for review: Brainard et al., 1999). Analytic action spectra, however, are superior to polychromatic action spectra for identifying the photopigments that mediate photobiological responses.

In a landmark study, Takahashi and colleagues determined an analytic action spectrum for circadian wheel running behavior in Syrian hamsters (Takahashi et al., 1984). Their study established fluence-response functions for a set of monochromatic wavelengths and then formed an action spectrum from those fluence-response functions. Their action spectrum had a spectral peak (max) around 500 nm and seemed similar in shape to the absorption spectrum for rhodopsin. Although they found these data to support the hypothesis that a rhodopsin-based photopigment and rod cells in the retina mediate circadian entrainment in hamsters, they were careful to point out that the participation of a cone mechanism could not be excluded. Since then, three other analytic action spectra have been published on circadian and neuroendocrine regulation in rodents. (Bronstein et al., 1987; Provencio and Foster, 1995; Yoshimura and Ebihara, 1996). Data from these action spectra have been fitted to spectral sensitivity curves for retinal-based visual photopigments. This curve fitting is predicated on the assumption that a retinal-based molecule transduces light stimuli for circadian regulation, and allows the prediction of the shape of the photopigment absorption spectrum as well as its peak sensitivity ($\lambda$ max). Across these rodent studies, the predicted $\lambda$ max ranges from 480 nm to 511 nm and is surrounded by a broad region of high sensitivity. From these studies, different photopigments have been suggested to be responsible for circadian regulation including rhodopsin, a rhodopsin-like molecule, a middle wavelength cone photopigment, or a UV cone photopigment. Furthermore, preliminary data from other investigators working with Takahashi, showed that the action spectrum for photoperiod-dependent reproductive development response of male Siberian hamsters and light-induced phase-shifting of circadian locomotor activity has its max in the range of 475 nm. The investigators interpret their unpublished action spectra to support the hypothesis that a short wavelength-sensitive photoreceptor mediates both functions. (Fred Turek, PhD, personal communication).

Circadian Regulation in Rodents with Loss of Cone and Rod Photoreceptors

It is important to note that there is considerable diversity in the cellular structure and function of the retina across mammalian species, and that in rodents the retina contains both cone and rod photoreceptors. (Rodieck, 1998). Early studies with blind mole rats and rats with destruction of retinal photoreceptors due to prolonged light exposure raised the possibility that neither the rods nor the cones used for vision participate in regulating the circadian and neuroendocrine systems. (Pevet et al., 1984; Webb et al., 1985). Despite profound loss of photoreceptors and vision, light detection for circadian and photoperiodic regulation was preserved. It remained possible, however, that a small population of surviving rods or cones could still be responsible for circadian photoreception.

Studies in mice with hereditary retinal disorders (rd/rd and rds/rds) have shown that these animals still exhibit normal light-induced melatonin suppression and circadian locomotor phase-shifts despite a nearly total loss of classical visual photoreceptors. The data support the conclusion that circadian photoreception is maintained either by 1) a very small number of rod or cone cells, or 2) an unrecognized class of retinal photoreceptors. (Foster et al., 1991; Provencio et al., 1994; Yoshimura et al., 1994). Further work with rd mice suggested that middle-wavelength sensitive (M-cones) and/or S-cones may be responsible for circadian photoreception. (Provencio and Foster, 1995; Yoshimura and Ebihara, 1996). Recent studies with transgenic coneless (cl) mice which have extensive loss of M-cones and S-cones show that these mice exhibit normal sensitivity for light-induced melatonin suppression and circadian phase-shifting of locomotion. (Lucas et al., 1999; Freedman et al., 1999). Similarly, coneless, rodless mice (rd/rd cl) also appeared to exhibit normal sensitivity for light-induced melatonin suppression and phase-shifting of wheel-running behavior. These results indicate that rods, M-cones and S-cones are not required for circadian photoreception. Removal of the eyes however, abolished light-induced circadian phase-shifting. (Freedman et al., 1999). Overall the results suggest that the mouse eye contains specific photoreceptors for circadian regulation different from the visual photoreceptors. A study on normal rats, however, shows that the rod and cone photoreceptors for vision provide input to SCN neurons. (Aggelopoulos and Meissl, 2000). Thus, it is premature to rule out the visual photoreceptors from playing a role in circadian regulation in animals with normal, intact eyes.

If the rods and cones that mediate vision in rodents are not the photoreceptors for circadian regulation in rodents, what are the alternative candidates? Recent studies with various vertebrate species have identified several new molecules which may serve as circadian photopigments. These putative photopigments include both opsin-based molecules such as vertebrate ancient (VA) opsin (Soni and Foster, 1997), melanopsin (Provencio et al., 1998), and peropsin (Sun et al., 1997) as well as non-opsin molecules like biliverdin (Oren, 1996) and cryptochrome (Miyamoto and Sancar, 1998). Among these new photopigments, only melanopsin has been specifically localized to the human neural retina (Provencio et al., 2000) and cryptochrome has been localized to the mouse neural retina (Miyamoto and Sancar, 1998). The molecular identification of these candidate photoreceptors and their localization in the retina and/or neural components of the circadian system, make them well-suited to act as circadian phototransducers.

In summary, the present invention involves a light system for stimulating or regulating neuroendocrine, circadian, and photoneural systems in mammals based upon the discovery of peak sensitivity ranging from 425-505 nm. Also, the present invention involves a light meter system for quantifying light which stimulates mammalian circadian, photoneural, and neuroendocrine systems, wherein the light meter has at least one light metering device to match peak wavelength sensitivity of mammalian photoreceptors for mammalian circadian, photoneural, and neuroendocrine systems. Furthermore, the present invention exploits this peak wavelength sensitivity for novel light systems, novel translucent and transparent materials, and novel lamps or other light sources with or without filters. The present invention also involves the peak sensitivity as the focal point for treatment of mammals with a wide variety of disorders or deficits, including but not limited to, light responsive disorders, eating disorders, menstrual cycle disorders, non-specific alerting and performance deficit, hormone-sensitive cancers, and cardiovascular disorders.

DEFINITIONS

"Light responsive disorders" means any disorder responding to or preventable by phototherapy and includes, but is not limited to, seasonal affective disorders, sleep disorders, circadian disruption, eating disorders, menstrual cycle disorders, non-specific alerting or performance deficits, hormone-sensitive cancers (including, but not limited to, breast cancers), and cardiovascular disorders.

"Light system" means a lamp, a lamp with filters, or another system or source for delivering light.

"Translucent or transparent material component" or "translucent or transparent material" includes, but is not limited to, at least one of the following: glasses, visors, windows, contacts, and filters. These materials may shape natural or artificial light.

"Light source" includes, but is not limited to, at least one of the following light sources: artificial light, natural light, and lamps.

SUMMARY OF THE INVENTION

The present invention involves a light system for stimulating or regulating neuroendocrine, circadian, and photoneural systems in mammals based upon the discovery of peak sensitivity ranging from 425-505 nm. Also, the present invention involves a light meter system for quantifying light which stimulates mammalian circadian, photoneural, and neuroendocrine systems, wherein the light meter has at least one light metering device to match peak wavelength sensitivity of mammalian photoreceptors for mammalian circadian, photoneural, and neuroendocrine systems, said peak wavelength ranging between 425-505 nm. Furthermore, the present invention exploits this peak wavelength sensitivity for novel light systems, novel translucent and transparent materials, and novel lamps or other light sources with or without filters. The present invention also involves exploiting this peak sensitivity for treatment of mammals with a wide variety of light responsive disorders or deficits, including but not limited to, light responsive disorders, eating disorders, menstrual cycle disorders, non-specific alerting and performance deficit, hormone-sensitive cancers, and cardiovascular disorders.

The light metering device is specifically configured to accurately quantify electromagnetic radiation that stimulates or regulates the circadian, photoneural, and neuroendocrine systems of healthy mammals or mammals having a variety of disorders. The meter's wavelength sensitivity matches the wavelength sensitivity of the photoreceptors for circadian, photoneural, and neuroendocrine regulation in mammals. This device is also used to quantify electromagnetic radiation which is optimum for treating Seasonal Affective Disorders (SAD) or other light-responsive disorders.

DETAILED DESCRIPTION

Figure 1:
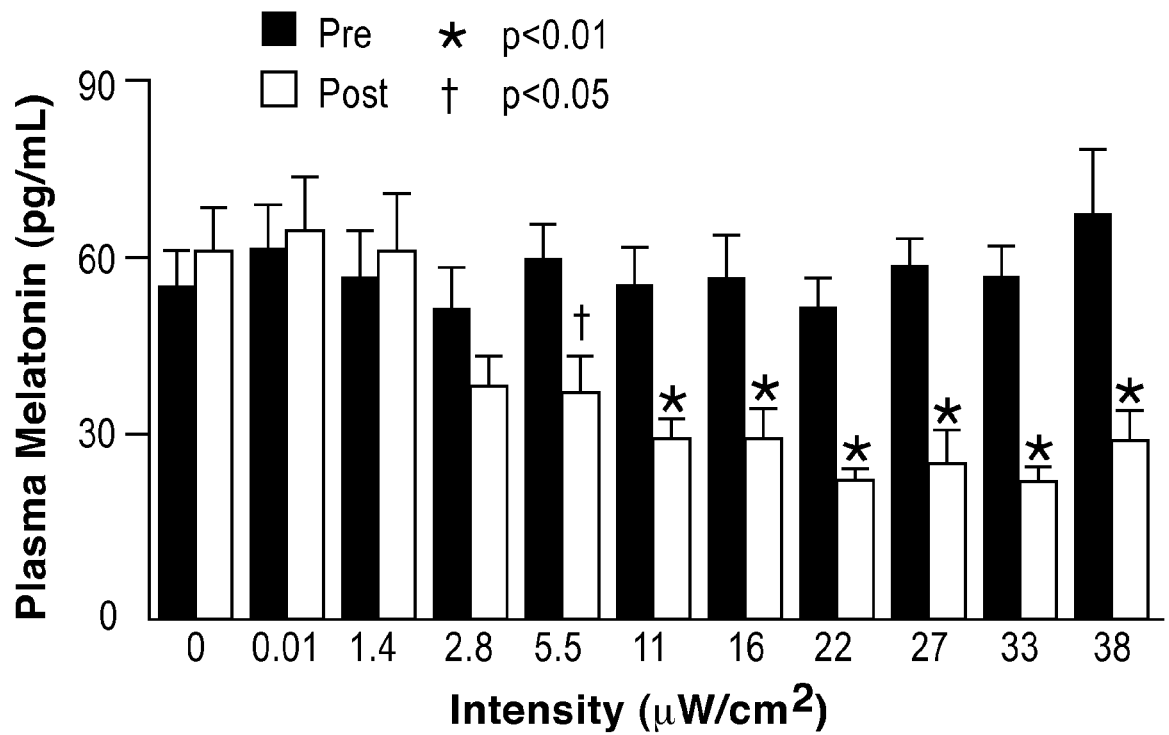
FIG. 1: In this graph the bars represent group mean +SEM plasma melatonin values (N=8) before and after monochromatic light exposure at 505 nm. There were no significant variations across mean melatonin pre-light exposure values (F=0.85). Paired, two-tailed Students' t tests demonstrated which light intensities elicited a significant melatonin suppression.

The science of photobiology involves the study of how the infrared, visible and ultraviolet portions of the electromagnetic spectrum influence biological processes. There are two broad categories of light measurement techniques: radiometric and photometric. Each measurement technique has its merits and drawbacks relative to circadian regulation, neuroendocrine regulation and light therapy. Radiometry is based exclusively on the physical properties of light—its energy and wavelength. A radiometer measures the radiant power of a light source over a defined range of wavelengths. Radiometers can be configured to measure different bandwidths across the electromagnetic spectrum. The wavelengths within the designated bandwidth can be detected equally, or they can be filtered for differential sensitivity across the various wavelengths.

In contrast to radiometry, photometry is based on the selective responsiveness of the human visual system. A photometer is simply a radiometer that has filters added to the detector which "shape" the detector sensitivity to resemble the luminance (brightness) response of the human visual system. Thus, photometry is a special branch of radiometry. Between individual humans, there are substantial differences in visual responses. The average photopic and scotopic visual functions are defined with reference to the adaptive state of the rod and cone photoreceptors in the human retina. Radiometers can be filtered to detect only those relative proportions of wavelengths that comprise the photopic or scotopic visual response. Photometers will detect photopic lux or scotopic lux, respectively. Specifically defined, lux measures are measures of illuminance—the amount of light, or luminous flux, falling on a surface. One photopic lux is one lumen per square meter ($lm/m^2$). The new metering system is configured to measure a new lighting unit which could be called "circadian lux" as opposed to photopic lux or scotopic lux.

Most investigators have operated from the assumption that light therapy is mediated via a photoreceptive mechanism in the human eye as opposed to a photoreceptive mechanism in the skin or some other part of the body. The data of the present invention demonstrate that the photoreceptive mechanism for the circadian and neuroendocrine system or the photoreceptive mechanism that mediates light therapy is not identical to the photoreceptive system that mediates the sensory capacity of vision.

Subjects, Materials and Methods

Subjects

The healthy females (N=6) and males (N=10) in this study had a mean ±SEM age of 25.7±0.8 yrs, demonstrated normal color vision as measured by the Ishihara and Farnsworth Munsell D-100 tests (mean FM score: 64.2±11.5), had a stable sleeping pattern (mean wake-up time 7:30 AM±12 min), and signed an approved IRB consent document before participating.

Light Exposure Protocol

Each experiment began at midnight when subjects entered a dimly lit room (10 lux). One drop of 0.5% Cyclopentolate HCl was placed in each eye to dilate the pupils, and blindfolds were placed over subjects' eyes. Subjects remained sitting upright in darkness for 120 min. While still blindfolded and just prior to 2:00 AM, a blood sample was taken by venipuncture. During light exposure, each subject's head rested in an opthalmologic head holder facing a Ganzfeld apparatus that provided a concave, patternless, white reflecting surface encompassing the subject's entire visual field. The subjects were exposed to the light stimulus from 2:00 to 3:30 AM. During this 90 min exposure, subjects sat quietly, kept their eyes open and gazed at a fixed target dot in the center of the Ganzfeld dome. Subject compliance for keeping their eyes open and the subjects' pupil size were monitored by a miniature video camera. At 3:30 AM, a second blood sample was taken. Each subject was exposed to complete darkness from 2:00 to 3:30 AM on their control night and was tested with at least 6 days between each nighttime exposure. Plasma samples were assayed for melatonin by RIA. (Rollag, 1976). The minimum detection limit of the assay was 0.5 -2.0 pg/mL. Control samples had 8% and 14% intra-assay coefficients of variation.

Light Production and Measurement

Experimental light stimuli were produced by xenon arc lamps (Photon Technology Int'l, Inc., Princeton, N.J.) enclosed in a light-proof chamber and cooled by high-speed fans and water circulation. An exit beam of light from each source was directed by a parabolic reflector, and excess heat in this beam was reduced by a water filter. Monochromatic wavelengths (10-11 nm half-peak bandwidth) were produced by a grating monochromator and light irradiance was controlled by a manual diaphragm. The resulting light beam was directed into the top area of a Ganzfeld dome and reflected evenly off the walls into volunteers' eyes. The entire reflecting surface of the dome was coated with a white surface with a 95-99% reflectance efficiency over the 400 to 760 nm range. Routine measurement of the light irradiance ($\mu W/cm^2$) was done with a J16 Meter with a 36512 irradiance probe (Tektronix, Beaverton, Oreg.). Experimental light stimuli reflected from the Ganzfeld domes were measured at volunteers' eye level immediately before and after the 90 min exposure. Additional measures were taken each half hour of the exposure to insure stimulus stability and enable intensity readjustment. Subjects in the 505 nm series were exposed to intensities ranging from 0.011 to 97 $\mu W/cm^2$ (a 3 log unit photon density range of $10^{10}$ to $10^{13}$ photons/$cm^2$). Subjects exposed to 555 nm received control or a 15 $\mu W/cm^2$ ($4.2\times10^{13}$ photons/$cm^2$) exposure.

Statistics

Two-tailed, Students' t tests were used to assess significance of raw melatonin change from 2:00 to 3:30 AM. These data were then converted to % control-adjusted melatonin change scores as described elsewhere. (Gaddy, 1993). For the 505 nm data, sets of pre-exposure melatonin values and % control-adjusted melatonin change scores were analyzed with one-way, repeated measures ANOVA. Significant differences between groups were assessed with post-hoc Scheffe F-tests; alpha was set at 0.05. For the 505 nm mean % control-adjusted melatonin suppression data, the computer program Origin 6.0 (Microcal, Northampton, Mass.) was used to fit a fluence-response curve to a 4 parameter model as described elsewhere (Brainard, 19893), and to test for goodness-of-fit of the data by coefficient of correlation.

Results

Figure 2:
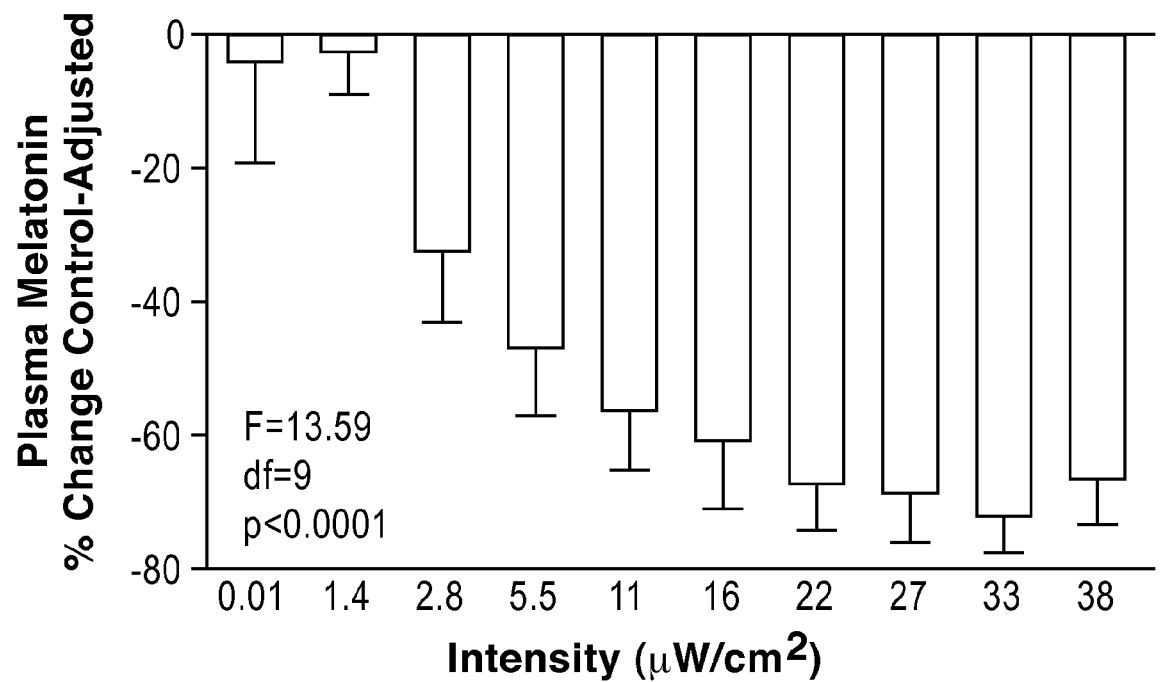
FIG. 2: This graph illustrates group mean +SEM % control-adjusted melatonin change values (N=8) at 505 nm monochromatic light exposure. The figure shows that progressively higher light irradiance exposure produces increasingly greater melatonin suppression.
Figure 3:
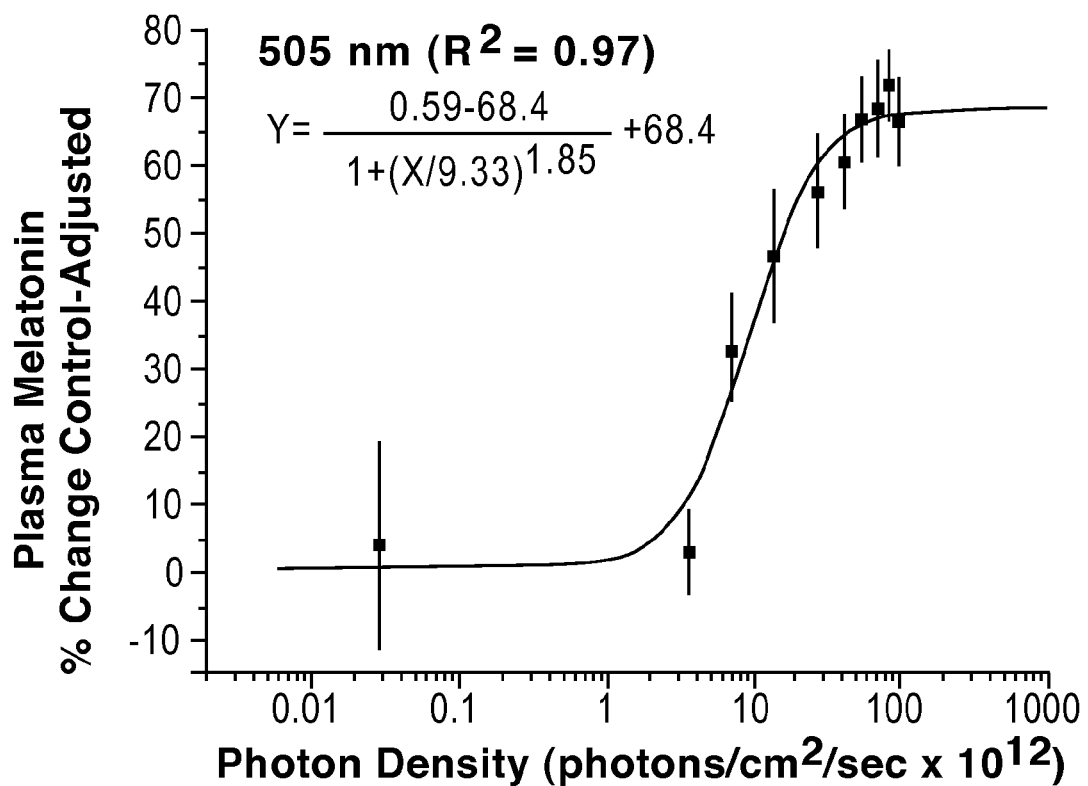
FIG. 3: This figure demonstrates the fitted fluence-response curve for photon density and % control-adjusted melatonin suppression (N=8). Each data point represents one group mean ±SEM.

The full 505 nm data complement, from raw melatonin values to a final fluence-response curve, is illustrated in FIGS. 1-3. Across all nights of testing, there were no significant differences (F=0.85) between sets of pre-exposure melatonin values indicating that plasma levels were consistent across the different study nights. FIG. 1 shows the mean ±SEM pre- and post-exposure melatonin values. One-way, repeated measures ANOVA showed a significant effect of light intensity on plasma melatonin % change scores (F=17.17, P<0.0001). Paired t tests demonstrated that compared to the 0 $\mu W/cm^2$ control night, all intensities at or above 5.5 $\mu W/cm^2$ significantly suppressed melatonin (P<0.05 or less). In contrast, irradiances of 2.8, 1.4 and 0.011 $\mu W/cm^2$ did not suppress melatonin compared to the control night (Scheffe F values: 0.97, 0.01 and 0.02, respectively). As illustrated in FIG. 2, all melatonin data were converted to control-adjusted % change scores. As with the melatonin % change scores, ANOVA showed a significant effect of light intensity on plasma melatonin % control-adjusted change scores (F=13.59, P<0.0001). FIG. 3 illustrates a best fit, sigmoidal fluence-response curve which plots melatonin % control-adjusted scores against stimulus photon density. The specific formula for this curve is included in the figure.

Figure 4:
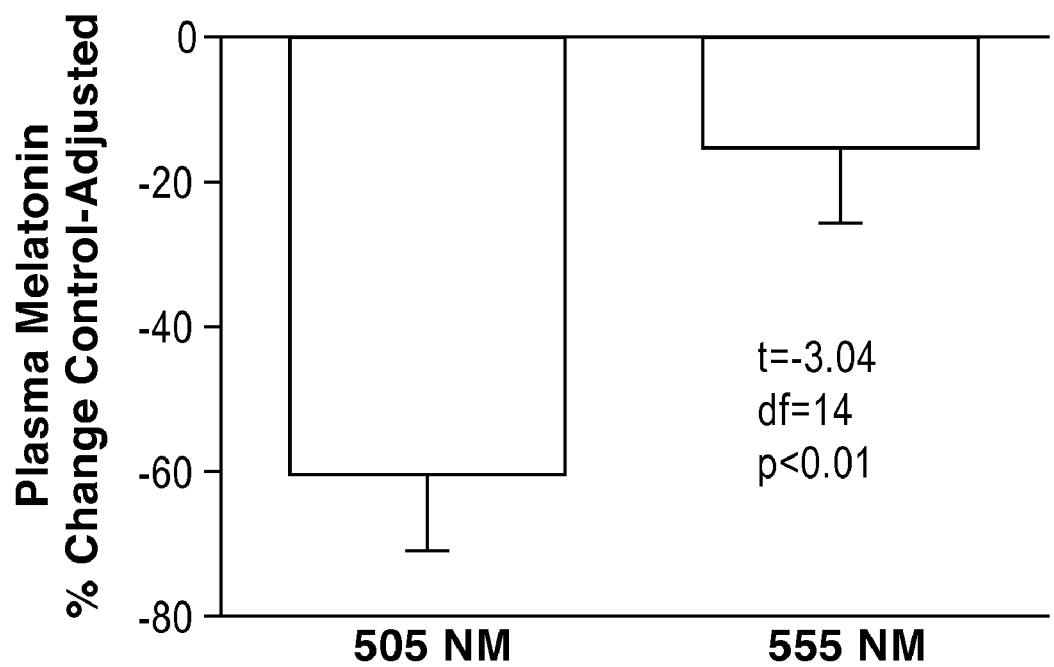
FIG. 4: The bars represent group mean+SEM values relative to an equal photon dose of $4.2 \times 10^{13}$ photons/cm$^2$. These data show that the 505 nm % control-adjusted plasma melatonin suppression is significantly stronger than that for 555 nm.

Subjects exposed to 555 nm received both control (0 μW/cm$^2$) and 15 μW/cm$^2$ (4.2×10$^{13}$ photons/cm$^2$) exposures. For the control and light exposure nights, the mean pre-exposure raw melatonin scores were 64.4±12.5 and 59.6±6.2, while the mean post-exposure scores were 62.6±10.5 and 49.1±6.0, respectively. The modest drop in melatonin over the 90 min 555 nm light exposure period was not statistically significant (t=1.69, df=7, P=0.14). For comparison of responses to 505 nm and 555 nm, FIG. 4 illustrates % control-adjusted melatonin suppression relative at equal photon densities across the two wavelengths. These data reveal that 505 nm is significantly stronger than 555 nm in suppressing melatonin (t=−3.04, df=14, P<0.01).

Discussion

The data presented here demonstrate that: 1) there is a clear fluence-response relationship between graded light intensities of 505 nm light and melatonin suppression, and 2) that 505 nm light is significantly stronger than 555 nm light for suppressing melatonin in healthy, human subjects. Previous studies with animals and humans have illustrated fluence-response relationships for melatonin suppression and circadian phase-shifting with exposure to monochromatic light (Podolin, 1987; Brainard, 1988; Nelson, 1991) as well as white light (Brainard, 1983; Boivin, 1996). A recent study on human subjects suggests that a four parameter curve is optimal for modeling light-induced melatonin suppression and circadian phase shifting. (Zeitzer, 1997). That contention matches earlier animal data (Brainard, 1983) as well as the 505 nm data reported here.

The demonstration that 505 nm light is more potent than 555 nm light for controlling melatonin has important basic science and clinical implications. In humans, it is well-established that higher levels of ocular illumination are required for stimulating the circadian system than for supporting vision. (Lewy, 1980, Nelson, 1991; Czeisler, 1986). Consequently, many investigators have considered the three cone photopic visual system to be responsible for stimulating circadian and neuroendocrine responses since this part of the visual system is responsive to "bright" daytime levels of illumination. Over the past 20 years most of the published literature on human circadian responses to light reports light levels in terms of illuminance (lux, lumens) which is a specific measure based on the traditional sensitivity curve of the photopic visual system. The peak wavelength sensitivity of that curve is 555 nm. (Rodieck, 1998). Indeed, some researchers have argued that their data support the notion that the visual cones are involved in circadian phase-shifting in humans. (Zeitzer, 1997). If melatonin regulation is mediated primarily by the three cone photopic visual system, then 555 nm light should be the most potent wavelength for regulating melatonin. The data here do not support this view. On the contrary, 505 nm is significantly stronger, photon for photon, than 555 nm in suppressing melatonin. The clinical implication of this result is that it is not optimum to use photometric values (lux) for quantifying light used therapeutically in patients with certain sleep disorders or circadian disruption due to shiftwork or intercontinental jet travel as is the current standard practice. (1995 Special Issue, J Biol).

Ultimately, these studies open the door for redefining how light should be measured relative to the circadian system. The best circadian measurement system would match the action spectrum for human circadian regulation. That action spectrum would not only elucidate the relative circadian potencies of different wavelengths, but it should help identify the photoreceptor that initiates signals from the retina to the SCN.

In summary, monochromatic 505 nm light suppressed melatonin in a fluence-response manner, and is approximately four times stronger than a 555 nm stimulus at an equal photon dose for melatonin suppression. These data demonstrate that the three cone system that is believed to mediate human photopic vision is not the primary photoreceptor system to transduce light stimuli for melatonin regulation.

Action Spectra Study Design

Action spectra are determined by comparing the number of photons required for the same biological effect at different wavelengths (Lipson, 1994; Coohill, 1999). The melatonin suppression action spectrum described here was formed from fluence-response curves at 8 wavelengths between 440 nm and 600 nm. A within-subjects design was used for each fluence-response curve. For each wavelength studied, a set of 8 volunteers was exposed to a minimum of 8 different light irradiances on separate nights with at least 6 days between exposures. At the completion of that work, it was determined that a probe of sensitivity to monochromatic light below 440 nm was needed. Consequently, a group of 8 subjects was exposed to a single night of no light exposure and a single night of exposure to one irradiance of 420 nm light.

Subjects

Volunteers who were involved in shift work, planned long distance jet travel before or during the study period, or had irregular sleeping schedules were excluded from this study. The subject drop-out rate was 7.9%. The ethnic distribution of the 72 subjects who completed this study included 55 Caucasians, 9 Asians, 4 African Americans, 3 Hispanics and 1 individual of unknown ethnicity. Subjects who had a relatively stable daily sleeping pattern, passed a physical exam for general and ocular health, and signed an approved IRB consent document were accepted into this study. A total of 37 females and 35 males between 18-30 years old (mean ±SEM age=24.5±0.3) completed the study. The self-reported mean±SE weekday wake-up time among subjects was 7:06 AM±18 min. All subjects were normal on the Ishihara and Farnsworth Munsell D-100 tests for color vision (mean ±SEM FM score: 51.4±4.3).

Light Exposure Protocol for Action Spectra

Each experiment began at midnight when subjects entered a dimly lit room (10 lux or less). One drop of 0.5% Cyclopentolate HCl was placed in each eye to dilate the subjects' pupils and blindfolds were placed over their eyes. Subjects remained sitting upright for 120 minutes and listened to music on headphones or engaged in quiet conversation. While still blindfolded and just prior to 2:00 AM, a 10 ml blood sample was taken by venipuncture of the antecubital vein. Subjects' blindfolds were then removed and the subjects were exposed to the monochromatic light stimulus from 2:00 to 3:30 AM. During light exposure, each subject's head rested in an opthalmologic head holder facing a ganzfeld apparatus that provided a concave, patternless reflecting surface encompassing each subject's entire visual field (see FIG. 1). During this 90 minute exposure, subjects sat quietly, kept their eyes open and gazed at a fixed target dot in the center of the ganzfeld dome. Subject compliance for keeping their eyes open and the subjects' pupil size were monitored by a miniature video camera inside the ganzfeld dome. If the subjects began to close their eyes during the exposure period, the experimenters reminded them to keep their eyes completely open. At 3:30 AM, a second 10 ml blood sample was taken by venipuncture and the subjects were then permitted to leave the laboratory. Eight wavelengths were studied for this action spectrum (440, 460, 480, 505, 530, 555, 575 and 600 nm). Across these wavelengths, each subject was exposed to complete darkness from 2:00 to 3:30 AM on their control night and to a set of irradiances covering a 4 log unit photon density range of $10^{10}$ to $10^{14}$ photons/cm$^2$ on exposure nights. For the probe of sensitivity to monochromatic light at 420 nm, a group of 8 subjects were exposed to a single night of no light exposure and a single night of exposure to 420 nm light at 31.8 µW/cm$^2$ (5.58×$10^{13}$ photons/cm$^2$).

Light Production and Measurement

Figure 5:
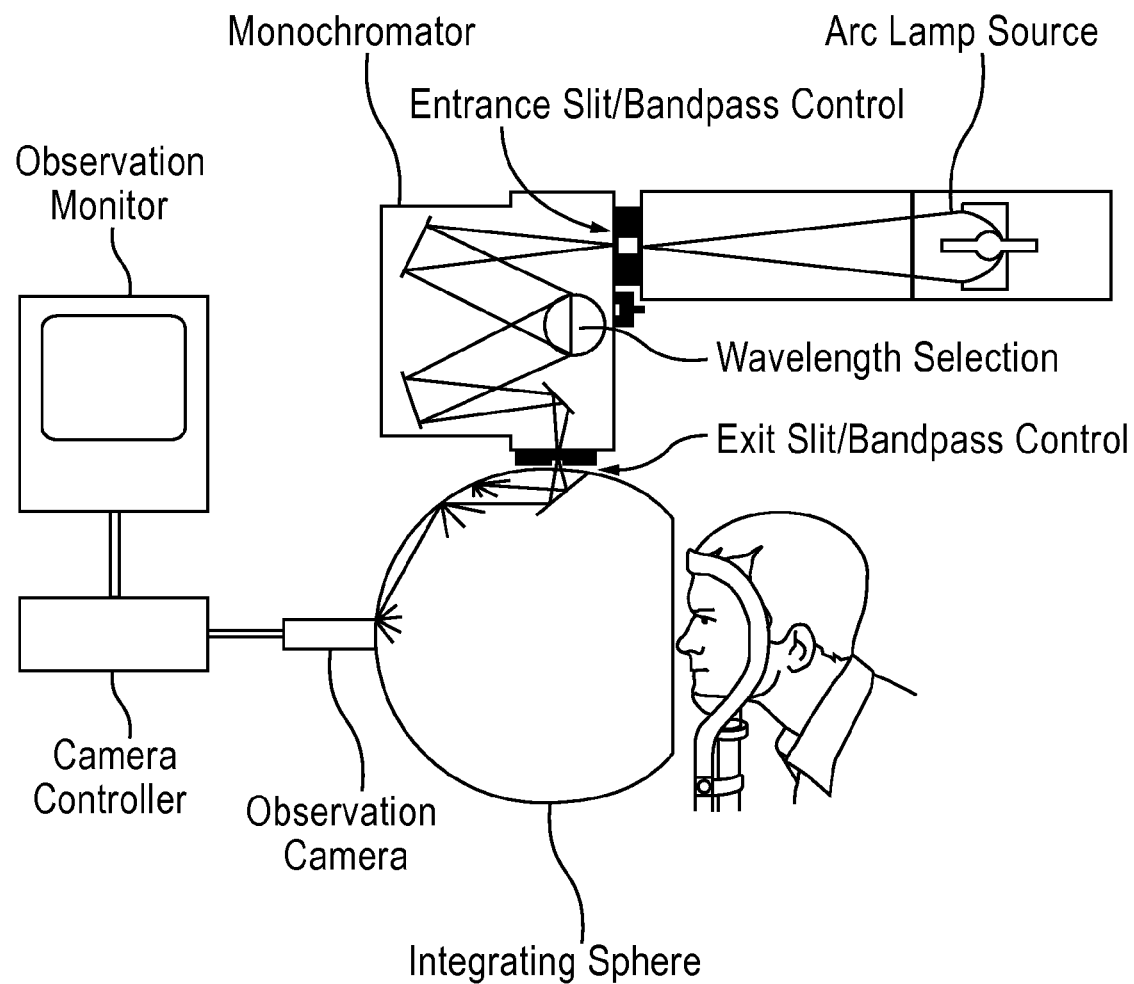
FIG. 5: This diagram illustrates the experimental electronic, optic and ganzfeld dome exposure array. This apparatus provides a uniform, patternless stimulus that encompasses the subject's entire visual field. For clarity, the subject's head is shown slightly withdrawn from the opening of the ganzfeld dome. During all light exposures, the subjects' bony orbits are completely enclosed in the dome walls providing complete exposure of their visual fields.

As shown in FIG. 5, experimental light stimuli were produced by a 450 or 1200 W xenon arc lamp (Photon Technology Inc., Princeton, N.J.). Each lamp was enclosed in a light proof chamber and cooled by water circulation. An exit beam of light from each source was directed by a parabolic reflector and, for the 1200 W lamps, excess heat in the light beam was reduced by a water filter. Monochromatic wavelengths (10-14.5 nm half-peak bandwidths) were produced by a grating monochromator and light irradiance was controlled by a manual diaphragm. The resulting light beam was directed into the top area of a ganzfeld apparatus and reflected evenly off the walls of the ganzfeld dome into volunteers' eyes. The entire reflecting surface of the dome was coated with a white material (Spectralite) with a 95-99% reflectance efficiency over the 400 to 760 nm range. Routine measurement of the light irradiance (µW/cm$^2$) was done with a Tektronix J16 Radiometer/Photometer with a J6512 irradiance probe (Tektronix, Beaverton, Oreg.). Experimental light stimuli reflected from the ganzfeld dome was measured at volunteers' eye level immediately before and after the 90 minute exposure. Additional measures were taken each half hour of the exposure to insure stimulus stability and enable readjustment of the intensity if it varied. These spot measures were taken with a ft-1° meter (Minolta, Osaka, Japan). Spectroradiometric assessment of the monochromatic wavelengths at the level of subjects' corneas was done with a portable spectroradiometer with a fiber optic sensor (Ocean Optics S2000). This equipment was calibrated with a standard lamp traceable to the National Institute of Standards and Technology (NIST).

In action spectroscopy, it is critical that the measured light stimuli are representative of the stimuli which actually reach the photoreceptors that mediate the photobiological response. In studies on light regulation of the circadian system, factors which can modify the measured stimulus before it reaches the photoreceptors include head and eye motion, squinting and eye closure, pupillary reflexes, and light transduction through the ocular media (Gaddy et al., 1993; Brainard et al., 1997). Most of these factors are controlled in the experimental technique described above. Concerning light transmission through ocular media, the cornea and aqueous and vitreous humors normally transmit nearly 100% of visible wavelengths to the retina and do not change substantively as the eyes age (Boettner and Wolter, 1962). In contrast, the aging human lens develops pigmentation that attenuates the transmission of shorter visible wavelengths to the retina (Lerman, 1987; Brainard et al., 1997). In the present study, restricting the age of volunteers to 18-30 years controlled this factor. Measurements of mean transmittance of 36 postmortem human lenses in this age range showed relatively even transmission from 440 to 600 nm. In contrast, there was a mean 45% reduction in lens transmission at 420 nm compared to 460 nm (Brainard et al., 1997). Consequently, measured corneal light irradiances at 420 nm had to be adjusted to compensate for reduced stimulus transmission to the retina even in this relatively young study group.

Blood Samples and Melatonin Assay

Blood samples were collected in glass vacutainers which contained EDTA. Plasma was separated by refrigerated centrifugation, aliquoted into cryogenic vials and stored at −20° C. until assay. Melatonin concentrations were assayed by radioimmunoassay using antiserum described by Rollag and Niswender, (1976). Radiolabeled ligand was prepared by adding 10 µl of a dioxane solution containing 1 µmole 5-methoxytryptamine and 1 µmole tri-N-butylamine to 250 µCi (0.1 nmole) dried Bolton-Hunter Reagent (New England Nuclear Corp., Boston, Mass.). The reaction was allowed to proceed for one hour before adding 50 µl of aqueous sucrose (16 gm/ml electrophoresis buffer) and purifying product by disc gel electrophoresis. Duplicate aliquots of 200 µl of each unknown and control sample were extracted into 2 ml of chloroform. The chloroform was removed in a SpeedVac centrifuge (Savant Instruments, Holbrook, N.Y.) and resuspended in 200 µl of assay buffer (phosphate buffered saline, pH 7.4, containing 0.1% gelatin with 100 mg thimerosal/liter as a preservative). The extracts were washed twice with 3 ml of petroleum ether, then evaporated to dryness in a SpeedVac before being resuspended in 200 µl of deionized water. Approximately 50,000 cpm of radiolabeled ligand and a 1:256,000 dilution of antiserum (R1055, Sep. 16, 1974) was added to each unknown and a triplicate 2-fold geometric series of standards ranging in concentration from 0.201 to 200 pg per 200 µl assay buffer. The final assay volume of buffer in each tube was 400 µl. At the end of the 48 hour incubation period, three ml of 95% ethanol (4° C.) was added to each assay tube and the bound radioactivity precipitated by centrifugation at 2000×g for 30 minutes. The supernatant was decanted and radioactivity in the precipitate was quantified. The quantity of melatonin immunoreactivity in the samples was calculated with the use of a computer program (M. L. Jaffe and Associates, Silver Spring, Md.; see Davis et al., 1980). All solutions were maintained at 4° C. throughout the radioimmunoassay procedure. Assay results were not corrected for recovery (which has proven to be >95% in independent trials). The minimum detection limit of the assay is 0.5-2.0 pg/ml.

Statistics for Action Spectra

Two-tailed, paired Student's t tests were used to assess statistical significance of raw melatonin change from 2:00 to 3:30 AM. Percent melatonin change scores were determined by the following formula:

$$\text{Percent Melatonin Change Score} = 100 \times \frac{03:30 \text{ h melatonin} - 02:00 \text{ h melatonin}}{02:00 \text{ h melatonin}}$$

Percent melatonin change scores then were normalized to percent control-adjusted change scores by subtracting the control (no light) condition percent change scores for each subject from that same subject's light exposure score. This technique accounts for the normal individual rise or fall in plasma melatonin levels with respect to the light-induced changes (Gaddy et al., 1993; Brainard et al., 1997). For data from each wavelength, complete sets of pre-exposure melatonin values, percent melatonin change scores, and percent control-adjusted melatonin change scores were analyzed with one way, repeated-measures ANOVA. Significant differences between groups were assessed with post-hoc Scheffe F-tests with alpha set at 0.05. The group of single fluence-response curves (one for each wavelength) was fitted to a parametric model in which the melatonin response (Y) to a photon dose (X) is predicted by: the theoretical initial Y-response (0 dose) for the curve ($A_1$); the theoretical final Y-response ("infinite" dose) for the curve ($A_2$); the dose producing a response halfway between $A_1$ and $A_2$ ($X_{50}$ or $ED_{50}$); and the slope estimator (p) for the slope of the curve between $A_1$ and $A_2$. The equation is:

$$Y = \frac{A_1 - A_2}{1 + (X/X_{50})P} + A_2$$

The computer program Origin 6.0 (Microcal, Northampton, Mass.) was used to fit the fluence-response curves to the data. From extensive experience in our laboratory, a saturating 90 minute light exposure produces a maximum mean percent control-adjusted plasma melatonin suppression ranging from 60 to 80% depending on the particular group of subjects being tested (Gaddy et al., 1993; Ruberg et al., 1996; Wang et al., 1999; Brainard et al., 2000; 2001). To form an analytical action spectrum, it is necessary to determine if all fluence-response curves can be fit to a univariant sigmoidal curve (Lipson, 1994; Coohill, 1991; 1999). To do this, sigmoid curves were fitted to the five fluence-response curves between 440 nm and 530 nm which reached a mean percent control-adjusted melatonin suppression of 60-80% by constraining the $A_1$ factor (theoretical initial Y-response) to 0 since no light exposure should yield a 0% control-adjusted plasma melatonin suppression. From this set of curves, a mean $A_2$ (theoretical final Y-response or "infinite" dose for the curve), and a mean p (slope estimator) was calculated. Subsequently, all 8 data sets (including the data sets which did not reach saturation) were then fitted to sigmoid curves that constrained $A_2$ and p to these means and constrained $A_1$ to 0. Each calculated curve was tested for goodness-of-fit of the data by coefficient of correlation.

Melatonin Action Spectrum

This action spectrum was formed from the photon density which elicited the half-saturation constant ($ED_{50}$) of the percent control-adjusted melatonin suppression for each of the 8 wavelengths. These half-saturation constants were derived from the 8 univariant fluence-response curves described above. The half-saturation constants were then normalized to the maximum response and plotted as relative sensitivity. The relative quantum sensitivity from each group of subjects was then graphically plotted (quanta/wavelength) to illustrate the resultant action spectra for melatonin suppression in humans. A predicted peak sensitivity for this action spectrum was determined by fitting a vitamin $A_1$-retinaldehyde photopigment template to the data by a modification of the method described by MacNichol (1983). Specifically, the long wavelength limb of vitamin $A_1$-based photopigments can be considered linear within the 10-90% sensitivity range when plotted on a frequency abscissa. To select the best fit vitamin $A_1$ template, the normalized 10-90% long wavelength melatonin $ED_{50}$ data were fitted to a series of vitamin $A_1$-based templates within the 10-90% sensitivity range of the templates' long-wavelength limbs (Partridge and De Grip, 1991). Pearson correlation coefficients derived from fitting the melatonin data to the templates indicated the optimum fitting template.

Results of Action Spectra

Variations in Pupillary Dilation Exposure Time and Melatonin Assay

Individuals vary slightly in their pupil size and response to mydriatic agents. Mean ±SD pupillary dilation was 7.19±0.88 mm for all 72 subjects across all nights of exposures. There were no significant pupil size changes during the light exposures. Similarly, there is a small degree of variability in exact light exposure durations due to slight experimental delays. Across 627 single-subject experiments, the mean±SD exposure duration was 90.6±2.1 minutes. A total of 53 assays were run to quantify melatonin in plasma samples collected during this project. Coefficients of variation calculated from control samples assayed as 19.2 pg/ml and 90.0 pg/ml had 10.8% and 4.0% for intra-assay coefficients of variation, respectively. The inter-assay coefficients of variation were 13.5% and 10.2%.

Fluence-Response Data at 460 nm

Figure 6:
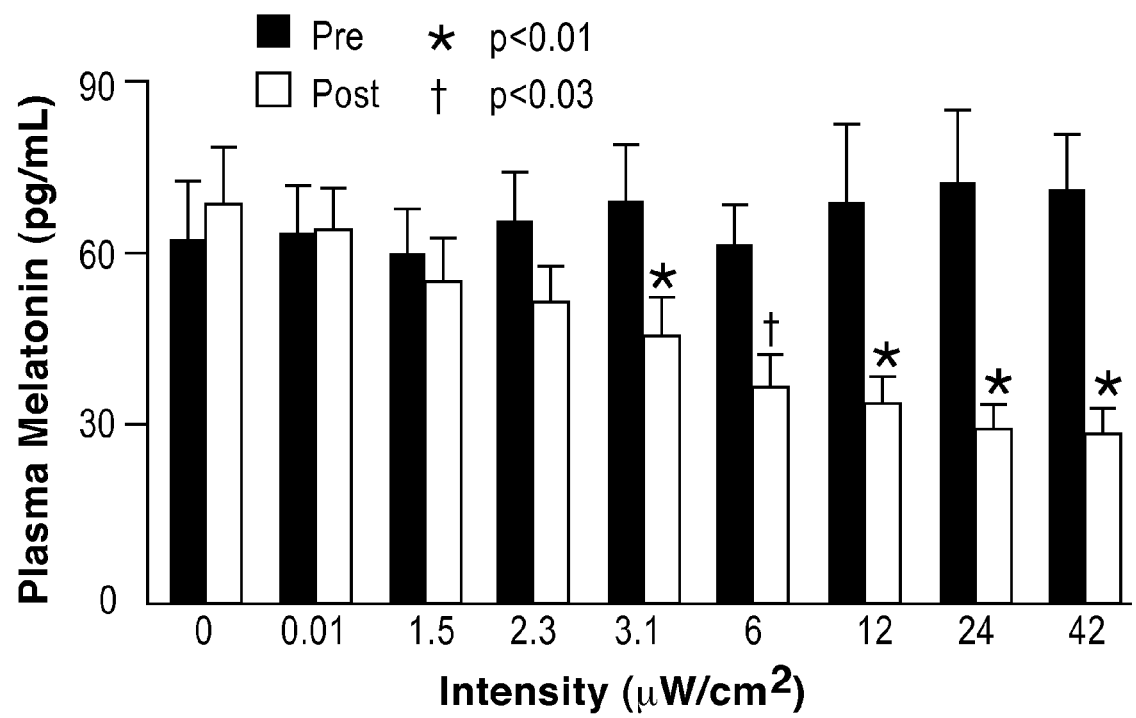
FIG. 6: In this graph the bars represent group mean+SEM plasma melatonin values before and after monochromatic light exposure at 460 nm in eight healthy subjects. There were no significant differences (F=0.70, p=0.69) across pre-exposure mean melatonin values. Light irradiances at or above 3.1 µW/cm$^2$ elicited significant melatonin suppression.

Since the predicted peak of the final action spectrum is 464 nm, the full data complement, from raw melatonin values to a final fluence-response curve for the nearby monochromatic stimulus at 460 nm, is illustrated in FIGS. 2-4. This fluence-response study at 460 nm was done with 8 subjects (4 males, 4 females). Across these subjects on all nights of testing, there were no significant differences (F=0.70, p=0.69) between sets of pre-exposure values indicating that baseline nocturnal melatonin levels were consistent across the different nights of study. FIG. 6 shows the mean+SEM pre- and post-exposure (2:00 to 3:30 AM) melatonin values (mean range 72.1-29.3 pg/ml). At 460 nm, exposure to irradiances of 2.3 µW/cm² and lower did not significantly suppress plasma melatonin. In contrast, exposures of 3.1 µW/cm² and higher elicited significant melatonin suppressions (p<0.03 or less).

Figure 7:
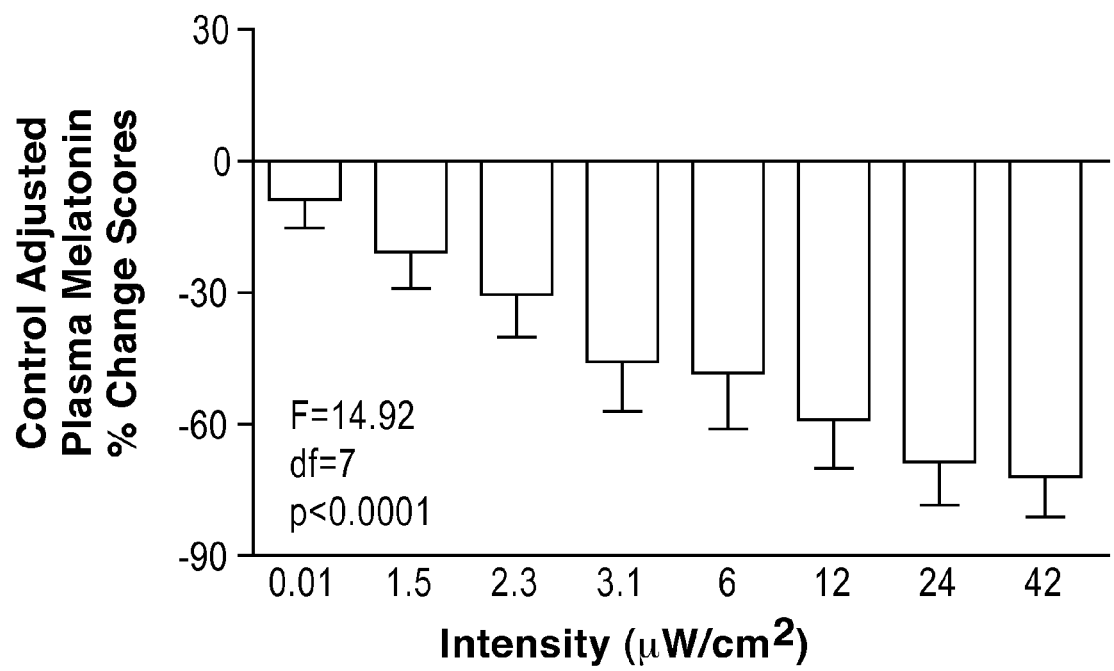
FIG. 7: This figure illustrates the mean+SEM plasma melatonin percent control-adjusted change scores from eight healthy subjects exposed to different irradiances of monochromatic light at 460 nm. Progressively higher irradiance exposures at 460 nm produce progressively greater plasma melatonin percent control-adjusted change scores (p<0.0001).

For comparative purposes, all melatonin data were converted to plasma melatonin percent control-adjusted change scores. As illustrated in FIG. 7, one-way, repeated measures ANOVA showed a significant effect of light intensity on plasma melatonin percent control-adjusted change scores (F=14.92, p<0.0001). Post-hoc tests on plasma melatonin percent control-adjusted scores demonstrated that all intensities at or above 3.1 µW/cm² significantly suppressed melatonin more than 0.012 µW/cm² (p<0.05 or less). Similarly, all irradiances at or above 12.1 µW/cm² significantly suppressed melatonin more than 1.5 µW/cm². Finally, both 24.2 and 42.2 µW/cm² exposures elicited significantly higher plasma melatonin percent control-adjusted change scores compared to an irradiance of 2.3 µW/cm².

The data from FIG. 7 can be mathematically converted into a best fit, sigmoidal curve which plots melatonin suppression against stimulus photon density. The specific formula for this curve is shown below and has a 0.97 coefficient of correlation ($R^2$).

$$y = \frac{7.17 - 73.4}{1 + (x/8.29)^{1.23}} + 73.4$$

Figure 8:
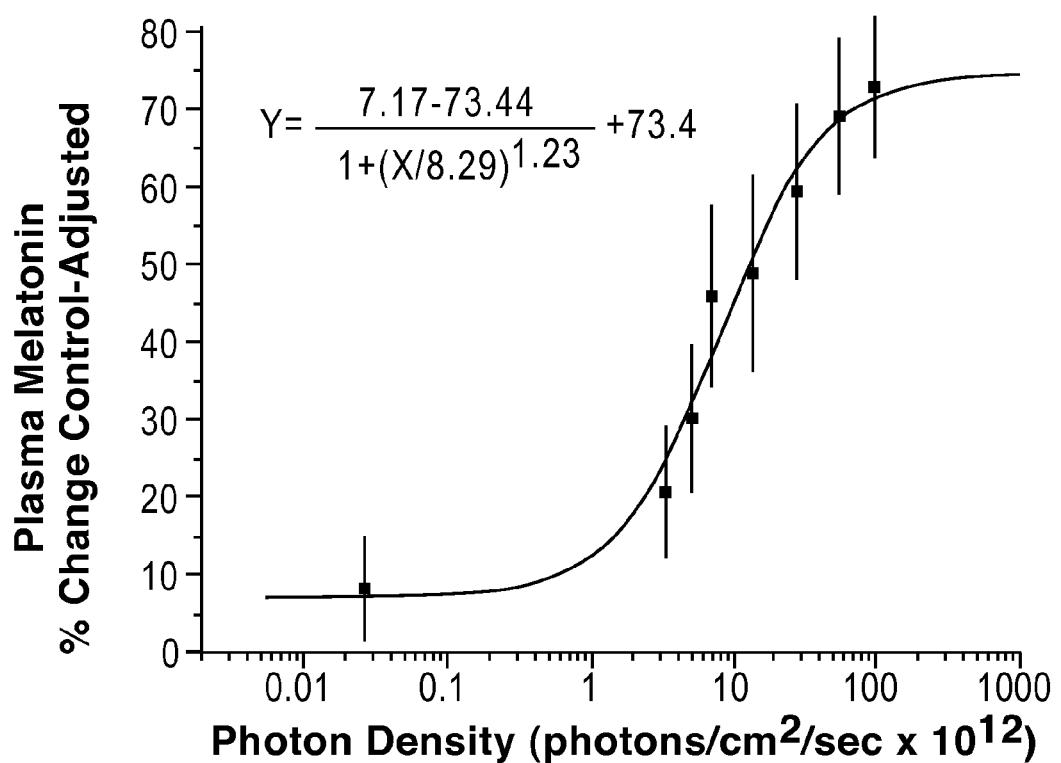
FIG. 8: This graph demonstrates the best fit fluence-response curve for 460 nm exposures and percent control-adjusted melatonin suppression (R$^2$=0.97). Each data point represents one group mean ±SEM from eight healthy subjects.
Figure 9A:
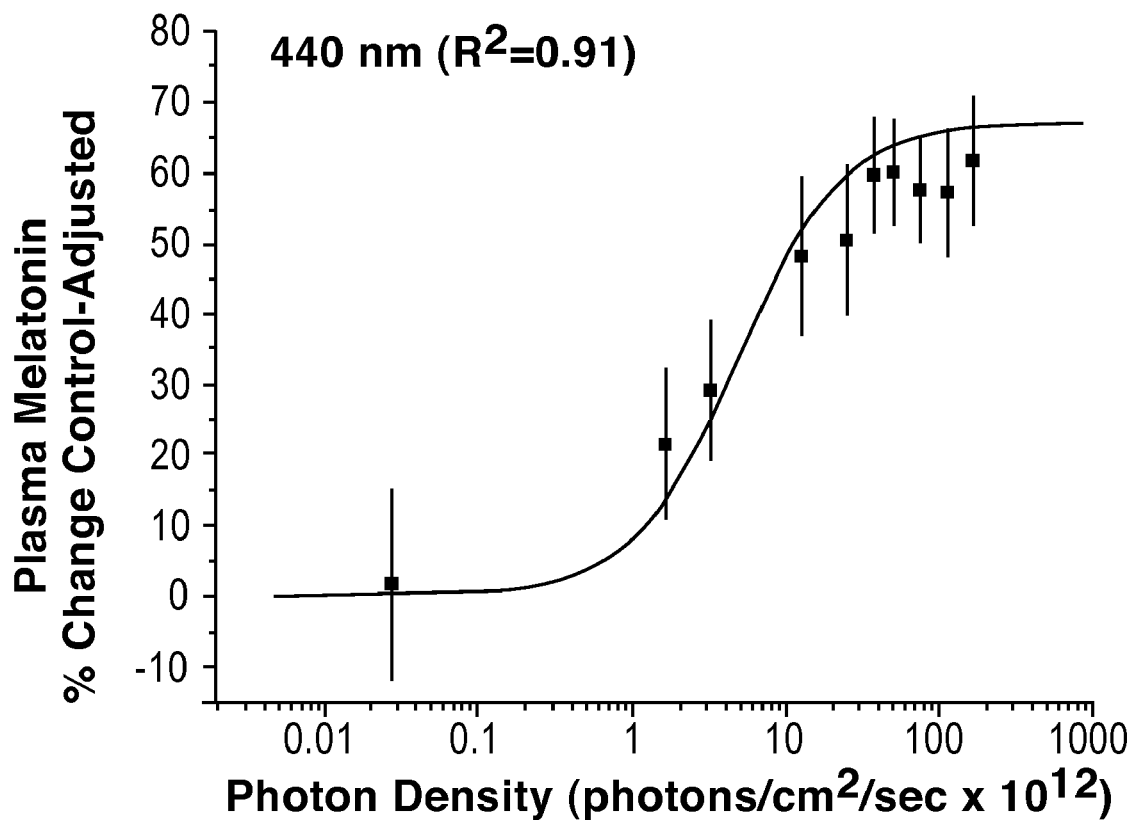
FIG. 9: This figure illustrates the fitted univariant fluence-response curves for monochromatic light exposures and percent control-adjusted melatonin suppression for eight wavelengths of visible light. Each fluence-response curve is derived from eight healthy volunteers who participated in a complete, within-subjects experimental design. In each graph, the data points represent group means ±SEM. Each curve has a high coefficient of correlation (0.95 to 0.81).
Figure 9B:
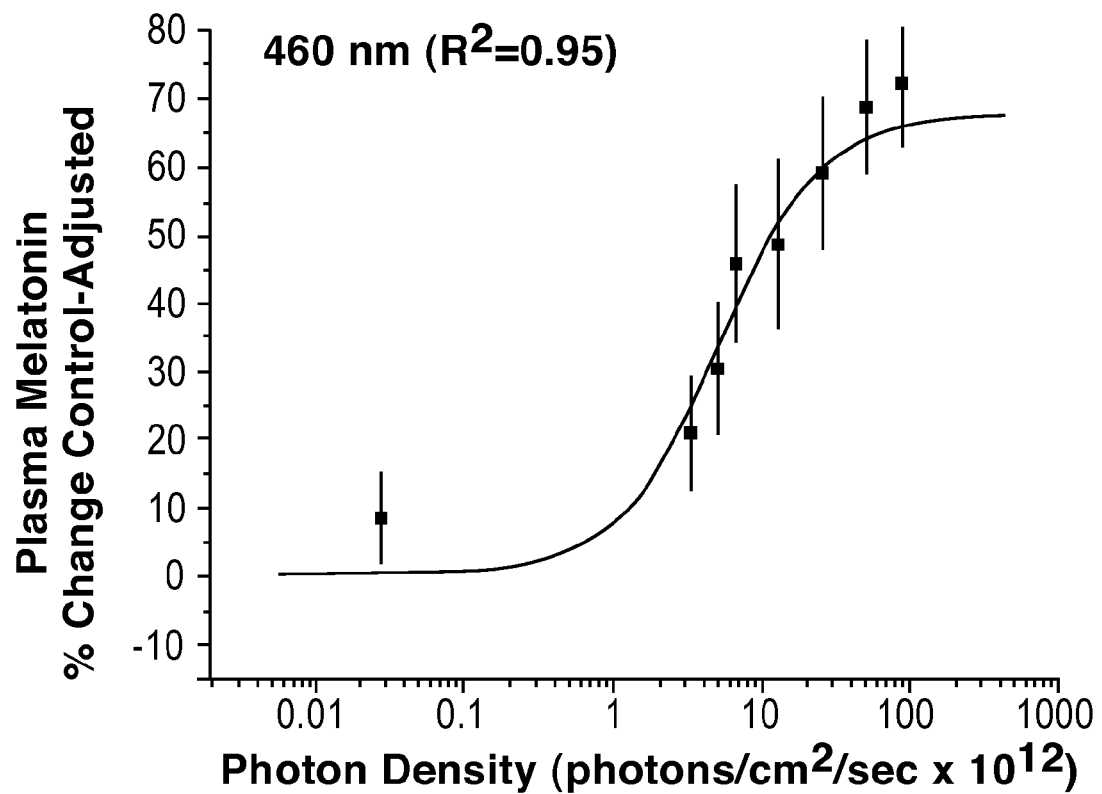
Figure 9C:
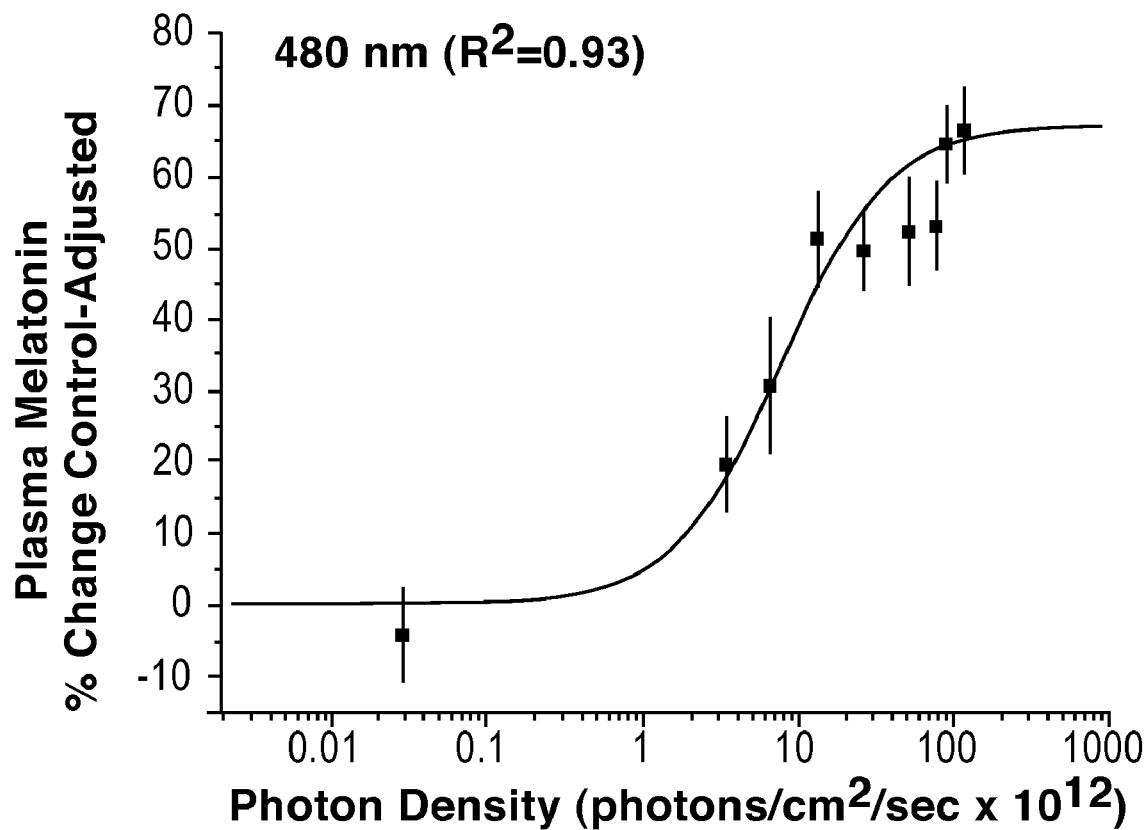
Figure 9D:
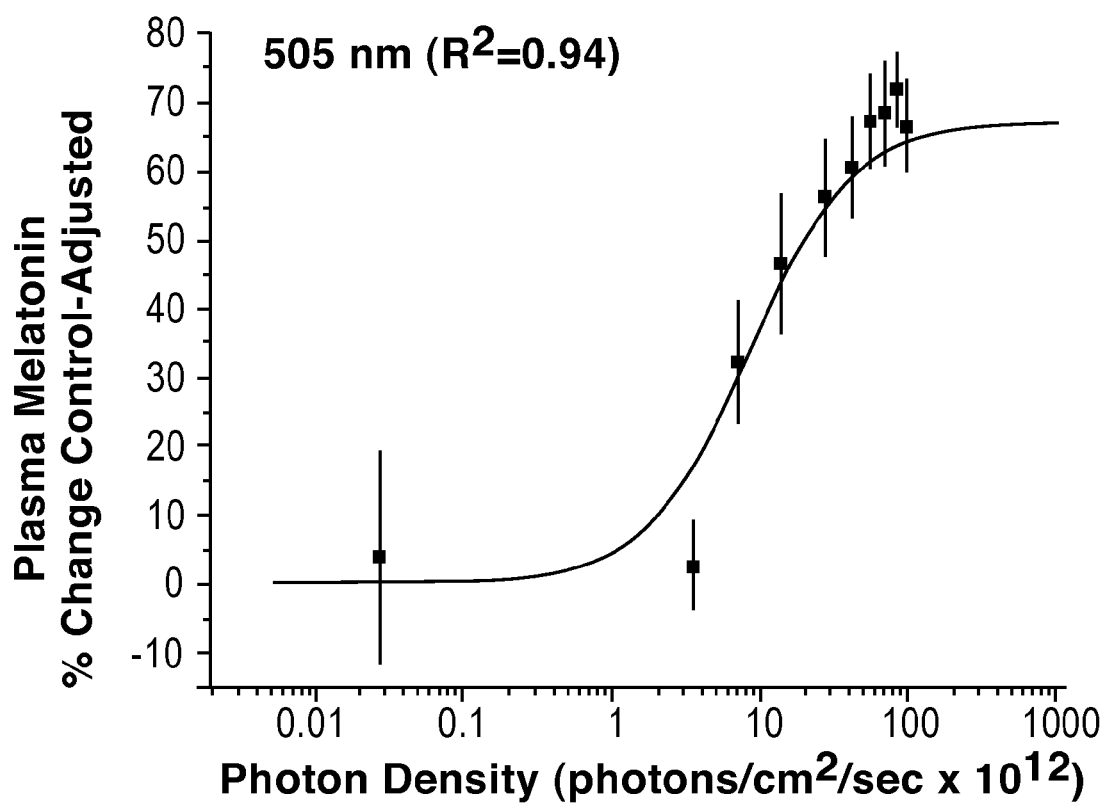
Figure 9E:
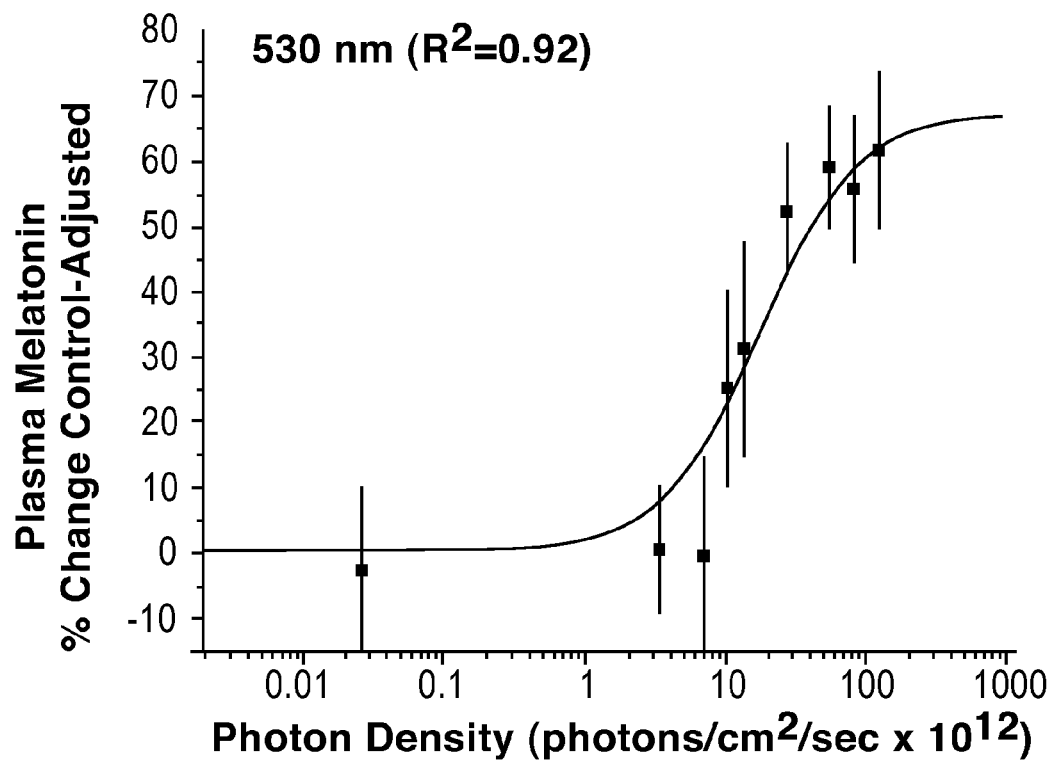
Figure 9F:
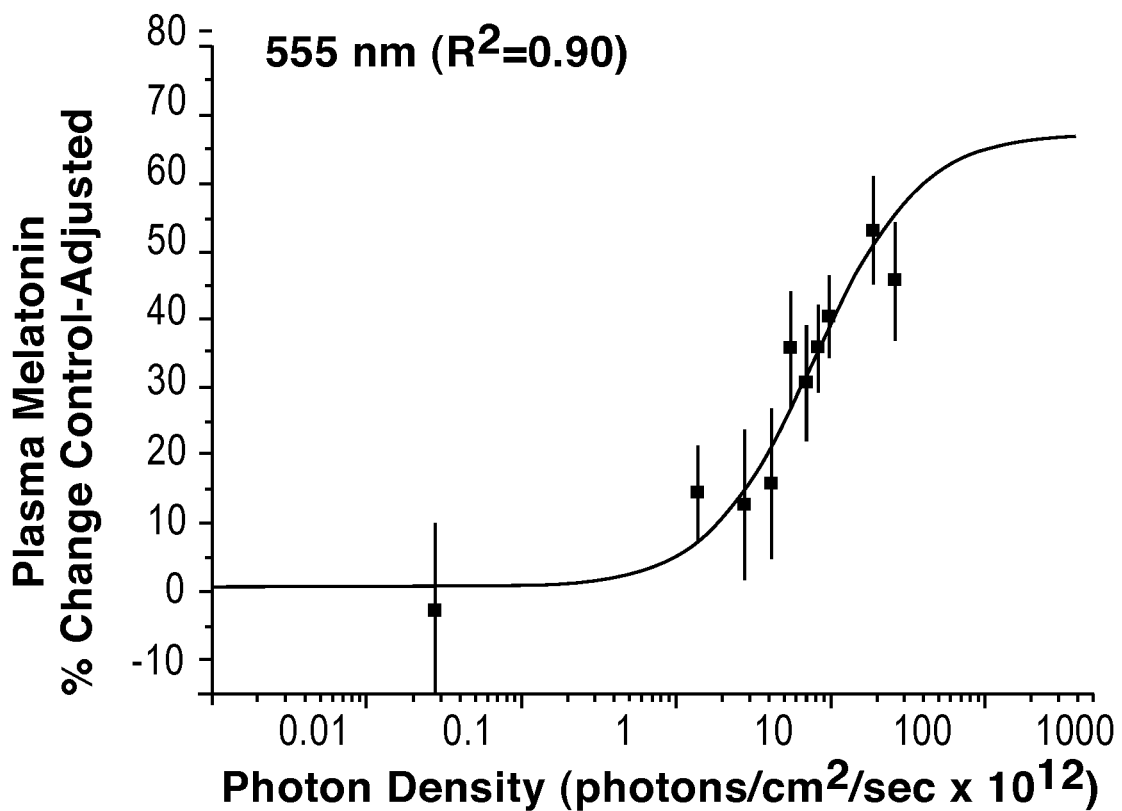
Figure 9G:
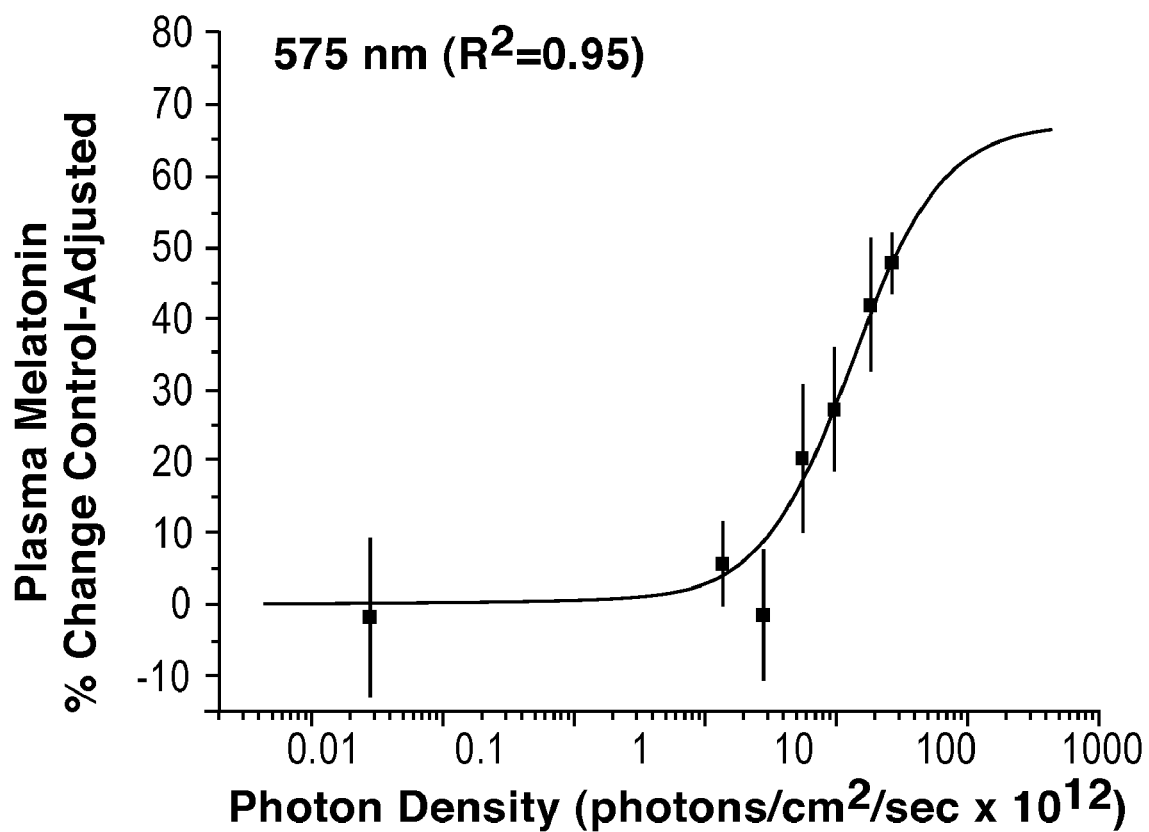
Figure 9H:
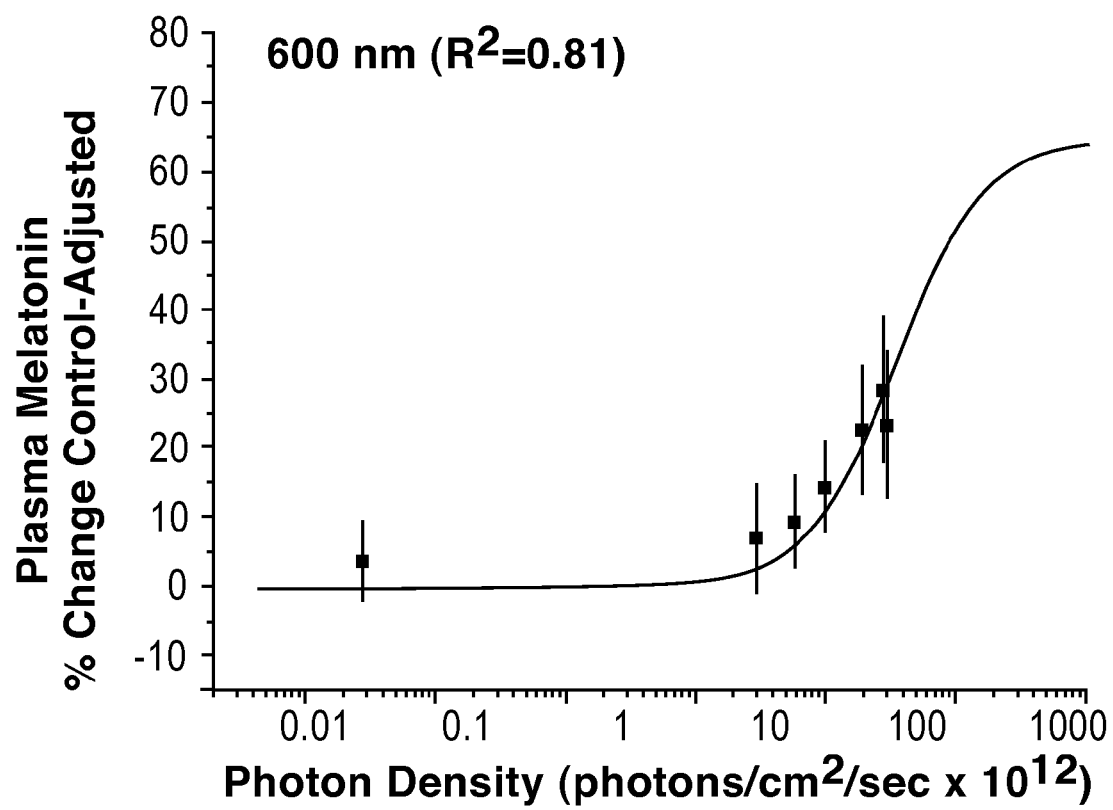

As shown in FIG. 8, this curve illustrates the fluence-response interaction between mean ±SEM melatonin percent control-adjusted change scores and the photon density of the monochromatic light.

Fluence-Response Data for All 8 Wavelengths

As shown in FIGS. 6-8, there is a clear, fluence-response relationship between graded photon densities of monochromatic 460 nm light and melatonin suppression. Data from each of the 8 wavelengths tested in this study fit four-parameter sigmoidal curves with high coefficients of correlation. Specifically, wavelengths at 440, 460, 480, 505, 530, 555, 575 and 600 nm had respective coefficients of correlation ($R^2$): 0.99, 0.97, 0.95, 0.97, 0.98, 0.92, 0.96, and 0.97. As described in the Methods, to form an analytical action spectrum, all fluence-response curves must be fit to a univariant sigmoidal curve (Lipson, 1994; Coohill, 1999). The univariant curve model for the data in this study has the factors of $A_1=0$, $A_2=66.9$, and $p=1.27$. FIG. 5 illustrates all 8 univariant fluence-response curves from this study. As with previous circadian analytical action spectra (Takahashi et al., 1984; Provencio and Foster, 1995; Yoshimura and Ebihara, 1996), full range fluence-response curves were not elicited above 550 nm. Despite this, standard photobiological curve fitting methods could be used to fit the data from all eight wavelengths in the present study to univariant, sigmoidal functions. When fit to a univariant fluence-response curve with these factors, the data from exposures to 440, 460, 480, 505, 530, 555, 575 and 600 nm have high coefficients of correlation of 0.91, 0.95, 0.93, 0.94, 0.92, 0.90, 0.95, and 0.81, respectively.

Melatonin Suppression Response to 420 nm at a Single Intensity

Figure 10:
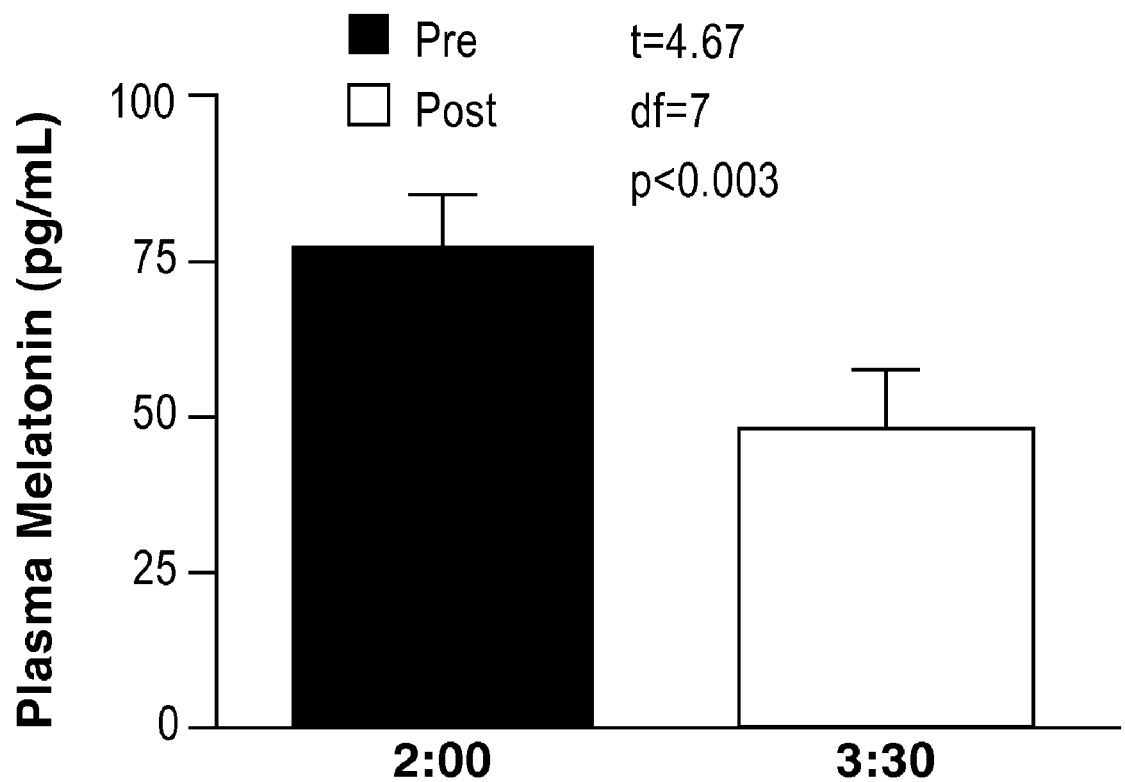
FIG. 10: In this graph the bars represent group mean+SEM plasma melatonin values before and after exposure to 31.8 µW/cm$^2$ monochromatic light at 420 nm in eight healthy subjects. This light irradiance induced a significant melatonin suppression (p<0.003).

Given the high sensitivity of subjects to short wavelength light as shown in FIG. 9, it was determined that a probe of sensitivity to monochromatic light below 440 nm was needed. On the control night when the eight volunteers were exposed to darkness only, their raw mean melatonin levels at 2:00 and 3:30 AM were 69.4 and 76.0 pg/ml, respectively. That small increase was not statistically significant ($t=-1.15$, $p=0.29$). As shown in FIG. 10, when these volunteers were exposed to 420 nm light at 31.8 $\mu W/cm^2$ ($5.58\times10^{13}$ photons/$cm^2$), raw mean melatonin levels at 2:00 and 3:30 AM were 76.4 and 47.6 pg/ml, respectively. That decrease in melatonin was statistically significant ($t=4.67$, $p<0.003$). For comparative purposes, this single melatonin suppression response was fitted to the univariant fluence-response curve formula used for all of the data in FIG. 9. The resulting curve estimated a half-maximum ($X_{50}$ or $ED_{50}$) melatonin suppression response for 420 nm of $1.83\times10^{13}$ photons/$cm^2$.

Action Spectrum for Melatonin Suppression

Figure 11:
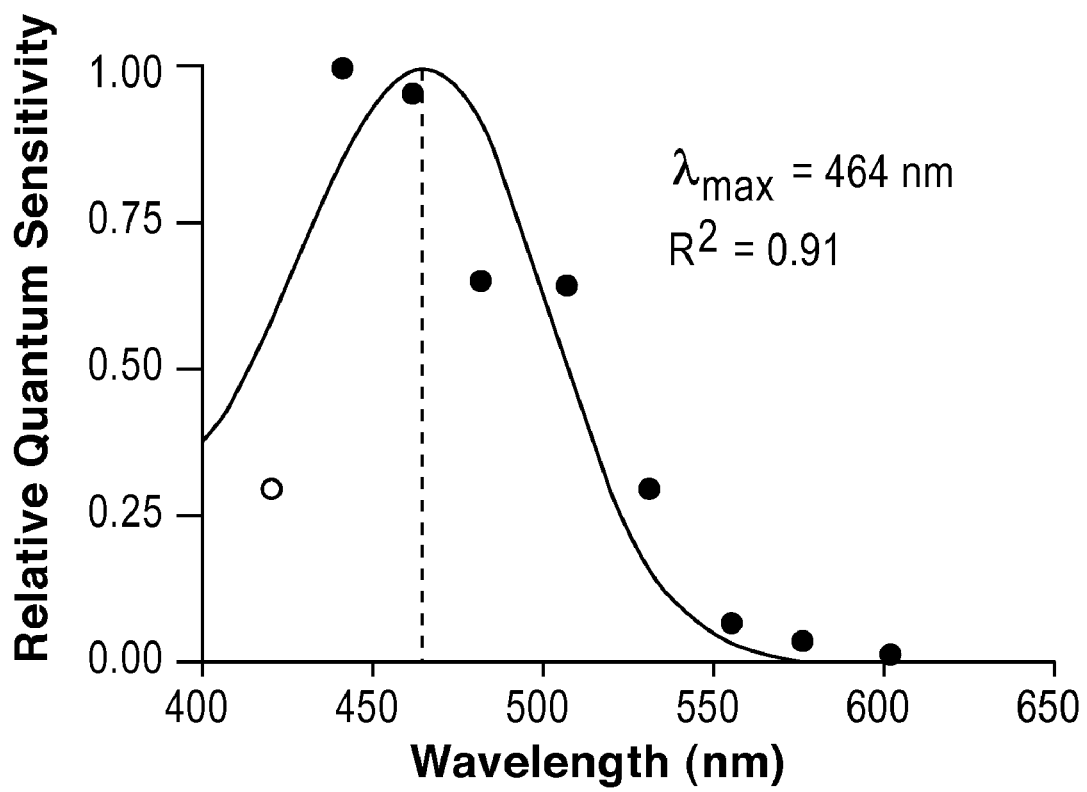
FIG. 11: This graph demonstrates the action spectrum for percent control-adjusted melatonin suppression in 72 healthy human subjects. The filled circles represent the half-saturation constants of eight wavelengths from 440 to 600 nm which were normalized to the maximum response and plotted as log relative sensitivity. The open circle represents the estimated half-saturation constant derived from the 420 nm data. The line in the graph portrays the best fit template for vitamin A$_1$ retinaldehyde photopigments which predicts a maximal spectral absorbance (1 max) of 464 nm (Partridge and De Grip, 1991). There is a high coefficient of correlation for fitting this opsin template to the melatonin suppression data (R$^2$=0.91). The basis for the balanced wavelength peak sensitivity range is a calculation of approximately two standard deviations from 464 nm.
Figure 12:
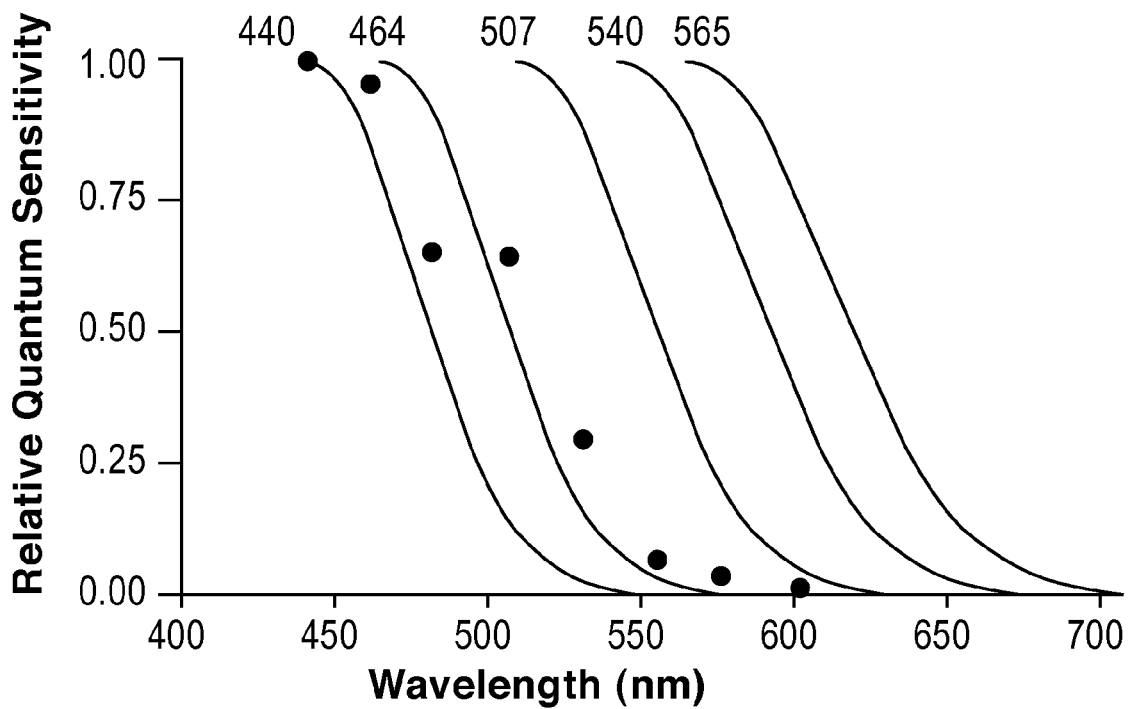
FIG. 12: This figure illustrates a comparison of the melatonin suppression and visual action spectra. The maximal spectral response and long wavelength limb of the melatonin suppression template is plotted along with the maximal spectral response and long wavelength limbs of the human rods and cones that support vision (Stockman and Sharpe, 1999). The shaded area around the 464 nm template represents±SD from the data presented above.

Action spectra are determined by comparing the number of photons required for the same biological effect at different wavelengths (Smith, 1989; Coohill, 1999). For this experiment, the action spectrum was formed from the photon density which elicited the half-saturation constant ($X_{50}$ or $ED_{50}$) of the percent control-adjusted melatonin suppression for each of the eight wavelengths. The half-saturation constants were derived from the eight univariant fluence-response curves shown in FIG. 9 and the one estimated half-saturation constant from the data shown in FIG. 10. The relative quantum sensitivity from each group of subjects was plotted in FIG. 11 (quanta/wavelength) to illustrate the resultant action spectra for human melatonin suppression. When the data were aligned to the best-fit template for vitamin $A_1$-retinaldehyde photopigments, this action spectrum predicted a peak spectral sensitivity (1 max) of 464 nm. There was a strong coefficient of correlation between the data and this fitted opsin nomogram ($R^2=0.91$).

Comparison of Action Spectra

The action spectrum for the photoreceptor system which provides input to the pineal gland appears to be distinct from the action spectra for the classical human visual photoreceptor systems. To illustrate this, the maximal spectral absorbencies and long wavelength limbs of the human rod and cone photoreceptors that support vision (Stockman and Sharpe, 1999) are illustrated in FIG. 8 along with the maximal spectral absorbence and long wavelength limb of the melatonin action spectrum. The shaded area around the melatonin action spectrum illustrates ±SD for this function.

Discussion of Action Spectra

The action spectrum presented here is based on univariant fluence-response curves for melatonin suppression by eight monochromatic light wavelengths in healthy subjects. These data fit a vitamin $A_1$ opsin template with 446-477 nm providing the strongest circadian input for melatonin regulation. These results suggest a novel photopigment in the human eye may be primarily responsible for melatonin regulation and may be distinct from the individual rod and cone photoreceptors for vision.

In developing a fluence-response curve, a complete within-subjects experimental design produces the most reliable results. When subjects are studied over a two to four month period, however, lack of stability in the subjects' circadian entrainment can introduce variability in light-induced melatonin suppression. This study accepted only volunteers who reported regular bed and wake times and their melatonin rhythms appeared to have been stable during the course of the study. As shown in the 2:00 AM melatonin values (FIG. 6), there were no significant differences between sets of pre-exposure values indicating that baseline melatonin levels were consistent across the different study nights. This phenomenon has been documented for the 505 nm fluence-response group as well as in other similarly controlled studies (Brainard et al., 1997; 2000; 2001; Wang et al., 1998). This within-subject stability of the melatonin rhythm over time has been frequently confirmed in the literature (Waldhauser and Dietzel, 1985; Arendt, 1988; 1998).

The data from each wavelength studied fit a univariant four parameter sigmoidal curve with a high coefficient of correlation. The univariance of these curves is consistent with, but does not prove, the hypothesis that melatonin suppression is modulated by a single photoreceptor type. Previous studies with animals and humans have illustrated similar fluence-response relationships for melatonin suppression and other circadian responses with monochromatic and broad spectrum light (Brainard et al., 1983; 1988; Podolin et al., 1987; McIntyre et al., 1989; Nelson and Takahashi, 1991; Zeitzer et al., 2000; Dkhissi-Benyahya et al., 2000). The initial attempts to define circadian and neuroendocrine responses to photons of different wavelength began with polychromatic action spectra which tested single irradiances of broader light bandwidths in various rodent species. These polychromatic action spectra were reasonably consistent in indicating that the spectral region between 450-550 nm provides the strongest stimulation of circadian and neuroendocrine responses in rodents (for review: Brainard et al., 1999). Analytic action spectra, based on sets of fluence-response curves at different monochromatic wavelengths, are superior for identifying photoreceptors that mediate photobiological responses (Lipson, 1994; Coohill, 1999).

There are four analytic action spectra on circadian and neuroendocrine regulation in hamsters, rats and mice (Takahashi et al., 1984; Bronstein et al., 1987; Provencio and Foster, 1995; Yoshimura and Ebihara, 1996). Data from these action spectra have been fitted to spectral sensitivity curves for retinal-based visual photopigments. This curve fitting is predicated on the assumption that a retinal-based molecule transduces light stimuli for circadian regulation, and allows the prediction of the shape of the photopigment absorption spectrum as well as its peak sensitivity (1 max). Across these studies which employed different circadian endpoints, the predicted 1 max ranges from 480-511 nm and is surrounded by a broad region of high sensitivity. From these results, different photopigments have been suggested to be responsible for circadian regulation, including rhodopsin, a rhodopsin-like molecule, a middle wavelength cone photopigment, or an ultraviolet cone photopigment.

It is commonly believed that the photopic visual system has a peak wavelength sensitivity around 555 nm (Rodieck, 1998). Many investigators have hypothesized that the photopic visual system mediates circadian and neuroendocrine responses, since this part of the visual system is responsive to "bright" daytime levels of illumination. Previous data (Brainard et al., 2001) and those presented above do not support this view. The results clearly demonstrate that 555 nm is significantly weaker in suppressing melatonin compared to an equal photon density of 460 nm. Thus, the photopic system is not likely to be the primary input for circadian regulation. Demonstrating that the photopic visual system is not the principal phototransducer for melatonin regulation does not preclude it from having any role in circadian input. Indeed, recent studies suggest that visual cones may be involved in circadian regulation. Recordings from SCN neurons in rats indicate that the visual rods and cones provide input to cells of the rat SCN (Aggelopoulos and Meissl, 2000). Similarly, a human phase-shifting study suggests that, under some circumstances, the visual long wavelength-sensitive cone may also mediate circadian vision in humans (Zeitzer et al., 1997).

The data presented here do not support the view that any of the known visual photoreceptors provide the primary input for melatonin regulation. FIG. 10 shows that none of the action spectra for individual visual photoreceptor systems match the action spectrum for melatonin suppression. If the photoreceptors that mediate vision in humans are not the primary photoreceptors for circadian regulation, what are the alternative candidates? Recent studies with various vertebrate species have identified several new molecules which may serve as circadian photopigments. These putative photopigments include both opsin-based molecules such as vertebrate ancient (VA) opsin (Soni and Foster, 1997), melanopsin (Provencio et al., 1998), and peropsin (Sun et al., 1997), as well as non-opsin molecules like biliverdin (Oren, 1996) and cryptochrome (Miyamoto and Sancar, 1998). Among these new photopigments, only melanopsin has been specifically localized to the human neural retina (Provencio et al., 2000) and cryptochrome has been localized to the mouse neural retina (Miyamoto and Sancar, 1998). Cryptochromes have been studied extensively as circadian photoreceptors in plants and insects (Ahmad and Cashmore, 1993; Stanewsky et al., 1998), and have been proposed as circadian photoreceptors in mammals (Miyamoto and Sancar, 1998; Thresher et al., 1998). The contention that cryptochromes serve as circadian photoreceptors in humans or other mammals, however, remains controversial (van der Horst et al., 1999; Griffin et al., 1999; von Schantz et al., 2000).

The action spectrum presented here matches a vitamin $A_1$-retinaldehyde photopigment template which supports the hypothesis that one of the new opsin photopigment candidates provides primary photic input for melatonin regulation in humans. The molecular identification of candidate opsin or non-opsin photoreceptors and their localization in the retina and/or neural components of the circadian system make them well-suited to act as circadian phototransducers.

Are the effects of light on melatonin suppression relevant to general circadian regulation? Studies have shown that hamsters have a higher intensity threshold for light-induced phase-shifts of wheel running rhythms than for melatonin suppression (Nelson and Takahashi, 1991). Recently, however, a study on humans showed that the 50% response sensitivity for circadian phase-shifting (119 lux) was only slightly higher than that for melatonin suppression (106 lux) with white light (Zeitzer et al., 2000). It is possible that there are separate photoreceptors for mediating circadian entrainment versus acute suppression of melatonin. It is reasonable, however, to conclude that a variety of non-visual effects of light such as melatonin suppression, entrainment of circadian rhythms, and possibly some clinical responses to light are mediated by a shared photoreceptor system.

In general, relatively high light illuminances ranging from 2,500 to 12,000 lux are used for treating winter depression, selected sleep disorders and circadian disruption (Wetterberg, 1993; Lam, 1998). Although these light levels are therapeutically effective, some patients complain that they produce side effects of visual glare, visual fatigue, photophobia, ocular discomfort, and headache. Determining the action spectrum for circadian regulation can lead to improvements in light therapy. Total illuminances for treating a given disorder can be reduced as the wavelength emissions of the therapeutic equipment are optimized.

Modern industrialized societies employ light extensively in homes, schools, work places and public facilities to support visual performance, visual comfort, and aesthetic appreciation within the environment. Since light is also a powerful regulator of the human circadian system, future lighting strategies will need to provide illumination for human visual responses as well as homeostatic responses. The action spectrum presented here suggests that there are separate photoreceptors for visual and circadian responses to light in humans. Hence, new approaches to architectural lighting may be needed to optimally stimulate both the visual and circadian systems.

In conclusion, this study characterizes the wavelength sensitivity of the ocular photoreceptor system for regulating the human pineal gland by establishing an action spectrum for light-induced melatonin suppression. The results identify 446-477 nm portion of the spectrum as the most potent wavelengths providing circadian input for regulating melatonin secretion. These data suggest that the primary photoreceptor system for melatonin suppression is distinct from the rod and cone photoreceptors for vision. Finally, this action spectrum suggests that there is a novel retinaldehyde photopigment which mediates human circadian photoreception. These findings open the door for optimizing the utilization of light in both therapeutic and architectural applications.

REFERENCES

Aggelopoulos N C, Meissl H (2000) Responses of neurones of the rat suprachiasmatic nucleus to retinal illumination under photopic and scotopic conditions. J Physiol 523: 211-222.

Ahmad M, Cashmore A R (1993) HY4 gene of *A. thaliana* encodes a protein with characteristics of a blue-light photoreceptor. Nature 366:162-166.

Arendt J (1988) Melatonin [Review]. Clin Endocrinol 29:205-229.

Arendt J (1998) Melatonin and the pineal gland: influence on mammalian seasonal and circadian physiology. Rev Reprod 3:13-22.

Boettner E A, Wolter J R (1962) Transmission of the ocular media. Invest Opthalmol Vis Sci 1:776-783.

Boivin D B, J F Duffy, R E Kronauer, C A Czeisler (1996) Dose-response relationships for resetting of human circadian clock by light. Nature 379: 540-542.

Brainard G C, Richardson B A, King T S, Matthews S A, Reiter R J (1983) The suppression of pineal melatonin content and N-acetyltransferase activity by different light irradiances in the Syrian hamster: a dose-response relationship. Endocrinology 113:293-296.

Brainard G C, Lewy A J, Menaker M, Miller L S, Fredrickson R H, Weleber R G, Cassone V, Hudson D (1988) Dose-response relationship between light irradiance and the suppression of melatonin in human volunteers. Brain Res 454: 212-218.

Brainard G C, Rollag M D, Hanifin J P (1997) Photic regulation of melatonin in humans: ocular and neural signal transduction. J Biol Rhythms 12:537-546.

Brainard G C, Greeson J M, Hanifin J P (1999) Action spectra for circadian and neuroendocrine regulation in mammals. In: Measurements of Optical Radiation Hazards (Matthes R, Sliney D, Didomenico S, Murray P, Phillips R, Wengraitis S, eds), pp 131-142. Munchen, Germany: ICNIRP.

Brainard G C, Rollag M D, Hanifin J P, van den Beld G, Sanford B (2000) The effect of polarized versus non-polarized light on melatonin regulation in humans. Photochem Photobiol 71:766-770.

Brainard G C, Hanifin J P, Rollag M D, Greeson J, Byrne B, Glickman G, Gerner E, Sanford B (2001) Human melatonin regulation is not mediated by the three cone photopic visual system. J Clin Endocrinol Metab 86:433-436.

Bronstein D M, Jacobs G H, Haak K A, Neitz J, Lytle L D (1987) Action spectrum of the retinal mechanism mediating nocturnal light-induced suppression of rat pineal gland N-acetyltransferase. Brain Res 406:352-356.

Coohill T P (1991) Action spectra again? Photochem Photobiol 54:859-870.

Coohill T P (1999) Photobiological action spectra—what do they mean? In: Measurements of Optical Radiation Hazards (Matthes R, Sliney D, Didomenico S, Murray P, Phillips R, Wengraitis S, eds), pp 27-39. Munchen, Germany: ICNIRP.

Czeisler C A, Shanahan T L, Klerman E B, Martens H, Brotman D J, Emens J S, Klein T, Rizzo J F, III (1995) Suppression of melatonin secretion in some blind patients by exposure to bright light. N Engl J Med 332:6-11.

Czeisler C A, Allan J S, Strogatz S H, Ronda J M, Sanchez R, Rios C D, Freitag W O, Richardson G S, Kronauer R E (1986) Bright light resets the human circadian pacemaker independent of the timing of the sleep-wake cycle. Science 233: 667-671.

Davis S E, Munson P J, Jaffe M L, Rodbard D (1980) Radioimmunoassay data processing with a small programmable calculator. Journal of Immunoassay 1:15-25.

Dkhissi-Benyahya O, Sicard B, Cooper H M (2000) Effects of irradiance and stimulus duration on early gene expression (fos) in the suprachiasmatic nucleus: temporal summation and reciprocity. J Neurosci 20:7790-7797.

Foster R G, Provencio I, Hudson D, Fiske S, DeGrip W, Menaker M (1991) Circadian photoreception in the retinally degenerate mouse (rd/rd). J Comp Physiol [A] 169: 39-50.

Freedman M S, Lucas R J, Soni B, von Schantz M, Munoz M, David-Gray Z, Foster R G (1999) Regulation of mammalian circadian behavior by non-rod, non-cone, ocular photoreceptors. Science 284:502-504.

Gaddy J R, Rollag M D, Brainard G C (1993) Pupil size regulation of threshold of light-induced melatonin suppression. J Clin Endocrinol Metab 77:1398-1401.

Goto M, Ebihara S 1990 The influence of different light intensities on pineal melatonin content in the retinal degenerate C3H mouse and the normal CBA mouse. Neurosci Lett. 108:267-272.

Griffin E A, Staknis D, Weitz C J (1999) Light-independent role of Cry1 and Cry2 in the mammalian circadian clock. Science 286:768-771.

Klein D C, Moore R Y, Reppert S M (1991) Suprachiasmatic Nucleus: The Mind's Clock. Oxford: Oxford University Press.

Klein D C, Weller J L (1972) Rapid light-induced decrease in pineal serotonin N-acetyltransferase activity. Science 177: 532-533.

Lam R W (1998) Seasonal Affective Disorder and Beyond: Light Treatment for SAD and Non-SAD Disorders. Washington, D.C.: American Psychiatric Press.

Lerman S (1987) Chemical and physical properties of the normal and aging lens: Spectroscopic (U V, fluorescence, phosphorescence, and NMR) analyses. Am J Opt Physiol Optics 64:11-22.

Lewy A J, Wehr T A, Goodwin F K, Newsome D A, Markey S P (1980) Light suppresses melatonin secretion in humans. Science 210:1267-1269.

Lipson E D (1994) Action spectroscopy: methodology. In: Organic Photochemistry and Photobiology (Horspool W M and Song P-S, eds), pp 1257-1266. New York: CRC Press.

Lucas R J, Foster R G (1999) Neither functional rod photoreceptors nor rod or cone outer segments are required for the photic inhibition of pineal melatonin. Endocrinology 140:1520-1524.

MacNichol E F, Levine J S, Mansfield R J W, Lipetz L E, Collins B A (1983) Microspectrophotometry of visual pigments in primate photoreceptors. In: Colour Vision (Mollon J D and Sharpe L T, eds), pp 14-38. Cambridge, England: Academic Press.

McIntyre I M, Norman T R, Burrows G D, Armstrong S M (1989) Human melatonin suppression by light is intensity dependent. J Pineal Res 6:149-156.

Miyamoto Y, Sancar A (1998) Vitamin B2-based blue-light photoreceptors in the retinohypothalamic tract as the photoactive pigments for setting the circadian clock in mammals. Proc Natl Acad Sci USA 95:6097-6102.

Moore R Y (1983) Organization and function of a central nervous system circadian oscillator: the suprachiasmatic hypothalamic nucleus. Federation Proceedings 42:2783-2789.

Moore R Y, Lenn N J (1972) A retinohypothalamic projection in the rat. J Comp Neurol. 146:1-14.

Morin L P (1994) The circadian visual system. Brain Res Brain Res Rev 19:102-127.

Nelson D E, Takahashi J S (1991) Comparison of visual sensitivity for suppression of pineal melatonin and circadian phase-shifting in the golden hamster. Brain Res 554: 272-277.

Oren D A (1996) Humoral phototransduction: blood is a messenger. The Neuroscientist 2:207-210.

Partridge J C, De Grip W J (1991) A new template for rhodopsin (vitamin A1 based) visual pigments. Vision Res 31:619-630.

Pevet P, Heth G, Hiam A, Nevo E (1984) Photoperiod perception in the blind mole rat (*Spalax ehrenbergi*, Nehring): involvement of the Harderian gland, atrophied eyes, and melatonin. J Exp Zool 232:41- 50.

Podolin P C, Rollag M D, Brainard G C (1987) The suppression of nocturnal pineal melatonin in the Syrian hamster: dose-response curves at 500 nm and 360 nm. Endocrinology 121:266-270.

Provencio I, Foster R G (1995) Circadian rhythms in mice can be regulated by photoreceptors with cone-like characteristics. Brain Res 694:183- 190.

Provencio I, Jiang G, De Grip W J, Hayes W P, Rollag M D (1998) Melanopsin: an opsin in melanophores, brain, and eye. Proc Natl Acad Sci USA 95:340-345.

Provencio I, Rodriguez I R, Jiang G, Hayes W P, Moreira E F, Rollag M D (2000) A novel human opsin in the inner retina. J Neurosci 20:600-605.

Reiter R J (1991) Pineal melatonin: cell biology of its synthesis and of its physiological interactions. Endocr Rev 12:151-180.

Rodieck R W (1998) The First Steps in Seeing, Sunderland, Mass.: Sinauer Associates, Inc.

Rollag M D, Niswender G D (1976) Radioimmunoassay of serum concentrations of melatonin in sheep exposed to different lighting regimens. Endocrinology 98:482-489.

Ruberg F L, Skene D J, Hanifin J P, Rollag M D, English J, Arendt J, Brainard G C (1996) Melatonin regulation in humans with color vision deficiencies. J Clin Endocrinol Metab 81:2980-2985.

Schwartz W J, Busis N A, Hedley-Whyte E T (1986) A discrete lesion of ventral hypothalamus and optic chiasm that disturbed the daily temperature rhythm. J. Neurol. 233:1-4.

Smith K C (1989) The Science of Photobiology. New York: Plenum Press.

Soni B G, Foster R G (1997) A novel and ancient vertebrate opsin. FEBS Lett 406:279-283.

Stanewsky R, Kaneko M, Emery P, Beretta B, Wager-Smith K, Kay S A, Rosbash M, Hall J C (1998) The cry mutation identifies cryptochrome as a circadian photoreceptor in drosophila. Cell 95:681-692.

Stockman A, Sharpe L T (1999) Cone spectral sensitivities and color matching. In: Color Vision From Genes to Perception (Gegenfurtner K R and Sharpe L T, eds), pp 53-87. Cambridge, United Kingdom: Cambridge University Press.

Sun H, Gilbert D J, Copeland N G, Jenkins N A, Nathans J (1997) Peropsin, a novel visual pigment-like protein located in the apical microvilli of the retinal pigment epithelium. Proc Natl Acad Sci USA 94:9893-9898.

Takahashi J S, DeCoursey P J, Bauman L, Menaker M (1984) Spectral sensitivity of a novel photoreceptive system mediating entrainment of mammalian circadian rhythms. Nature 308:186-188.

Thresher R J, Vitaterna M H, Miyamoto Y, Kazantsev A, Hsu D S, Petit C, Selby C P, Dawut L, Smithies O, Takahashi J S, Sancar A (1998) Role of mouse cryptochrome blue-light photoreceptor in circadian photoresponses. Science 282: 1490-1494.

van der Horst G T J, Muijtjens M, Kobayashi K, Takano R, Kanno S, Takao M, de Wit J, Verkerk A, Eker A P M, van Leenen D, Buijs R, Bootsma D, Hoeijmakers J H J, Yasui A (1999) Mammalian Cry1 and Cry2 are essential for maintenance of circadian rhythms. Nature 398:627-630.

von Schantz M, Provencio I, Foster R G (2000) Recent developments in circadian photoreception: more than meets the eye. Invest Opthalmol Vis Sci 41:1605-1607.

Waldhauser F, Dietzel M (1985) Daily and annual rhythms in human melatonin secretion: role in puberty control. Ann N Y Acad Sci 453:205-214.

Wang J Y, Hanifin J P, Rollag M D, Brainard G C (1999) Ocular regulation of the human pineal gland: the significance of total retinal exposure for melatonin suppression. In: Biologic Effects of Light 1998 (Holick M and Jung E G, eds), pp 367-374. Boston, Mass.: Kluwer Academic Publishers.

Webb S M, Champney T H, Lewinski A K, Reiter R J (1985) Photoreceptor damage and eye pigmentation: influence on the sensitivity of rat pineal N-acetyltransferase activity and melatonin levels to light at night. Neuroendocrinology 40:205-209.

Wehr T A (1991) The durations of human melatonin secretion and sleep respond to changes in daylength (photoperiod). J Clin Endocrinol Metab 73:1276-1280.

Wetterberg L (1993) Light and Biological Rhythms in Man. Stockholm: Pergamon Press.

Yoshimura T, Ebihara S (1996) Spectral sensitivity of photoreceptors mediating phase-shifts of circadian rhythms in retinally degenerate CBA/J (rd/rd) and normal CBA/N (+/+) mice. J Comp Physiol [A] 178:797-802.

Zeitzer J M, Kronauer R E, Czeisler C A (1997) Photopic transduction implicated in human circadian entrainment. Neurosci Lett 232:135-138.

Zeitzer J M, Dijk D-J, Kronauer R E, Brown E N, Czeisler C A (2000) Sensitivity of the human circadian pacemaker to nocturnal light: melatonin phase resetting and suppression. J Physiol 526:695-702.

1995 Special Issue: Task force report on light treatment for sleep disorder J Biol Rhythms 10: 99-176.

What is claimed is:

1. A system for measuring optical radiation, comprising:
a meter configured to measure circadian lux corresponding to a spectral sensitivity of a photoreceptor system for at least one of a circadian, photoneural or neuroendocrine system in a mammal, wherein the said circadian lux includes at least one peak within the range of approximately 425-505 nm, wherein said meter is configured to measure the therapeutically effective levels of the circadian lux; and
means for stimulating the photoreceptor system to treat or prevent at least light responsive disorder in said mammal.

2. The system of claim 1, wherein said meter is configured to measure therapeutically effective levels of the circadian lux.

3. The system of claim 2, further comprising a light source configured to generate circadian lux with a peak in the range of 425-505 nm.

4. The system of claim 3, further comprising a reflective dome configured to provide substantially uniform reflectance in the range of 400-760 nm.

* * * * *